(12) United States Patent
Gaudon et al.

(10) Patent No.: US 9,194,834 B2
(45) Date of Patent: Nov. 24, 2015

(54) CHEMORESISTOR TYPE GAS SENSOR HAVING A MULTI-STOREY ARCHITECTURE

(75) Inventors: Alain Gaudon, Launac (FR); Chang Hyun Shim, Toulouse (FR); Philippe Menini, Eaunes (FR); Francois Loubet, Avignonet Lauragais (FR)

(73) Assignees: ALPHA MOS S.A., Toulouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 2 days.

(21) Appl. No.: 14/124,342

(22) PCT Filed: Jun. 8, 2012

(86) PCT No.: PCT/EP2012/060922
§ 371 (c)(1),
(2), (4) Date: Dec. 6, 2013

(87) PCT Pub. No.: WO2012/168444
PCT Pub. Date: Dec. 13, 2012

(65) Prior Publication Data
US 2014/0105790 A1 Apr. 17, 2014

(30) Foreign Application Priority Data
Jun. 8, 2011 (EP) .................................. 11305707

(51) Int. Cl.
*G01N 15/06* (2006.01)
*G01N 33/00* (2006.01)
(Continued)

(52) U.S. Cl.
CPC .............. *G01N 27/16* (2013.01); *G01N 27/125* (2013.01); *G01N 27/128* (2013.01)

(58) Field of Classification Search
USPC .............. 422/50, 68.1, 83, 82.01, 98; 436/43, 436/181, 106, 139, 116, 117, 118
See application file for complete search history.

(56) References Cited

U.S. PATENT DOCUMENTS 4,495,793 A 1/1985 Hager
5,448,906 A 9/1995 Cheung
(Continued)

FOREIGN PATENT DOCUMENTS

DE 19831313 A1 1/2000
DE 102 45 947 B4 1/2007
(Continued)

OTHER PUBLICATIONS

International Search Report for corresponding PCT Application No. PCT/EP2012/060922, mailed Sep. 12, 2012.

*Primary Examiner* — Brian J Sines
(74) *Attorney, Agent, or Firm* — Workman Nydegger

(57) ABSTRACT

A multi-storey gas sensor is constructed by stacking chemoresistor type gas sensing elements and providing holes through each sensing element so gas can pass from one sensing element to the next, through the sensing layers. A rich data set can be obtained by selecting appropriate combinations of materials for the different sensing layers and varying the operating conditions of the different gas-sensing elements by: taking measurements when different combinations of sensing layers are activated, when given sensing layers are heated to different temperatures or according to different heating profiles, and/or when selected sensing layers are exposed to UV light. Sensor sensitivity and selectivity can be increased by applying UV pulses of controlled duration, and target gas species can be detected based on the transient response of the sensing layer at onset of UV irradiation. Each sensing element may have a micro-hotplate architecture.

11 Claims, 12 Drawing Sheets

(51) Int. Cl.
*G01N 33/48* (2006.01)
*G01N 27/16* (2006.01)
*G01N 27/12* (2006.01)

(56) References Cited

U.S. PATENT DOCUMENTS

| | | | |
|---|---|---|---|
| 6,918,284 B2* | 7/2005 | Snow et al. | 73/31.05 |
| 2003/0109056 A1* | 6/2003 | Vossmeyer et al. | 436/169 |
| 2005/0150778 A1 | 7/2005 | Lewis et al. | |
| 2009/0020422 A1 | 1/2009 | Ragahurama et al. | |
| 2009/0256215 A1* | 10/2009 | Novak et al. | 257/414 |
| 2011/0259080 A1 | 10/2011 | Ratcliffe et al. | |

FOREIGN PATENT DOCUMENTS

| | | |
|---|---|---|
| WO | 0004377 A1 | 1/2000 |
| WO | 2009037289 A1 | 3/2009 |

* cited by examiner

FIG.8
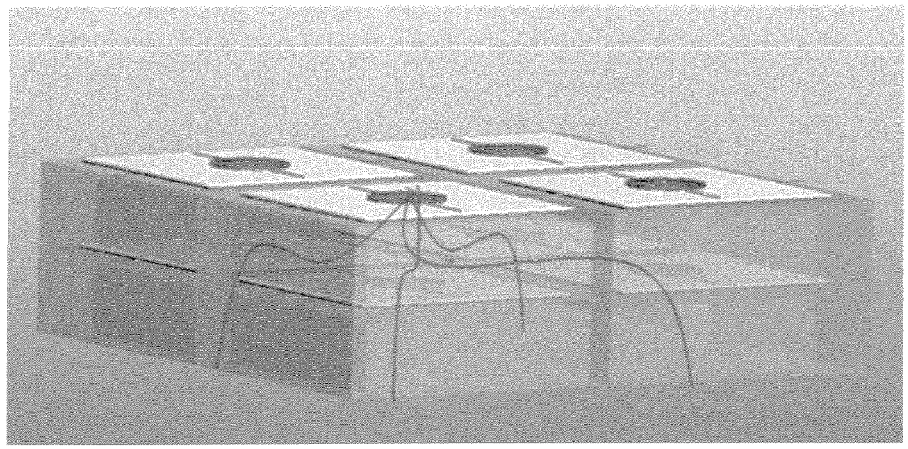
FIG.9 Schematic Diagram of Smart Gas Sensor Capsule
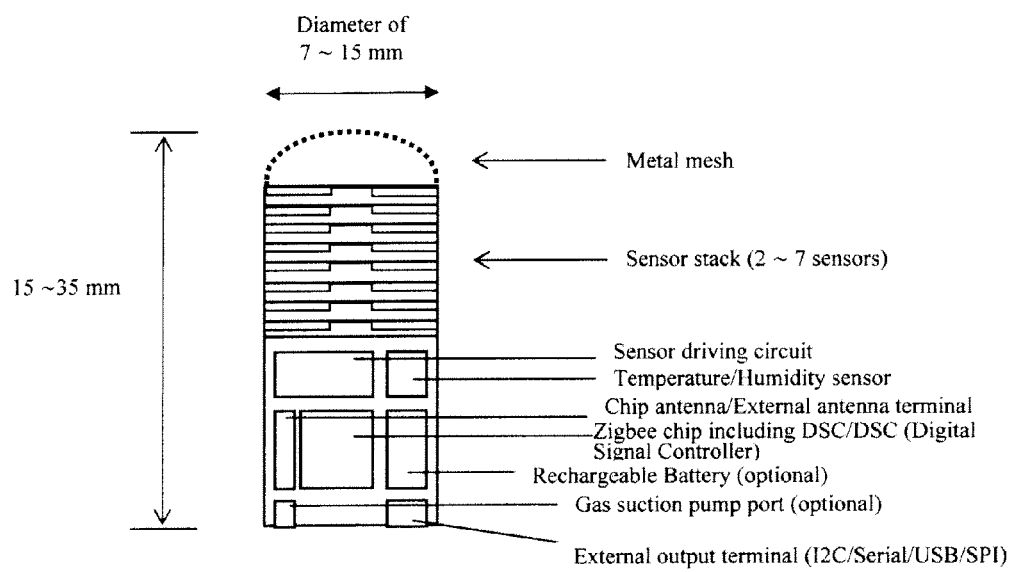
Applications
Smart phone, Indoor/outdoor air quality monitoring, Disease diagnosis, Smart mask, Intelligent Robot, Digital media instruments, Intelligent toys TIME X 10 (msec)

TIME X 10 (msec)

CHEMORESISTOR TYPE GAS SENSOR HAVING A MULTI-STOREY ARCHITECTURE

FIELD OF THE INVENTION

The present invention relates to the field of gas sensors and, more particularly, to gas sensors of chemoresistor type.

BACKGROUND OF THE INVENTION

Gas sensors are used in many applications, notably in situations where it is desired to detect or recognise a particular gas and in situations where it is desired to determine the composition of a gas mixture. In the present text, unless the context demands otherwise: the expression "gas" will be used to designate both a specific gas species and a mixture of different gaseous species, and the general expression "characterisation" will be used to designate both the process of recognizing or detecting a particular gas and the process of determining the composition of a gas. It is to be understood that references in this text to a "gas sample" generally include references to any gas which is presented to the gas sensor (whether as a discrete sample or by exposing the sensor to an ambient gaseous medium).

Gas sensors have been developed using different sensing technologies, including chemoresistor type gas sensors, such as those based on semi-conducting metal-oxides. FIG. 1 is a cross-sectional view which illustrates, schematically, the basic structure of a semi-conducting metal-oxide type gas sensor 1.

As shown in FIG. 1, a semi-conducting metal-oxide type gas sensor 1 has a sensing layer 2 made of semi-conducting metal-oxide provided on an insulating layer 3 supported on a base 4. When the sensor 1 is exposed to a gas, gas particles G may become adsorbed on the surface of the sensing layer 2, and oxidation-reduction reactions may occur, leading to a change in the impedance (conductance, capacitance, inductance or plural of these parameters) of the sensing layer 2. This change of impedance is measured using a pair of measuring electrodes 5 provided in contact with the sensing layer 2. Often the measurement is made by applying a potential difference across the measurement electrodes and monitoring how the impedance presented by the sensing layer changes. The waveform of the signal produced by the measuring electrodes is characteristic of the gas reacting with the sensing layer 2 and, typically, the waveforms produced by gases of interest are learned during a teaching phase preparatory to analysis of unknown gas samples.

In general, it is necessary to heat the sensing layer 2 to a relatively high temperature (notably 250° C. or above depending on the material forming the sensing layer and the gas species to be detected) for useful adsorption phenomena to be observed. Accordingly, typical gas sensors of this type also include a heater 6, as well as a temperature sensor (not shown in FIG. 1). After a measurement has been taken the heater 6 is activated to heat the active layer to a high temperature, above the usual operating temperature, so as to cause de-sorption of adsorbed particles, thus cleaning the sensor 1 ready for a subsequent measurement.

An aim in this field is to be able to construct micro-sensors, that is to say, miniaturized gas sensors particularly those that are small enough to be integrated into everyday appliances (for example, mobile telephones, face masks, intelligent toys, etc). It is a requirement for micro-sensors that they should have sufficiently high performance, that is, they should be able to detect a target gas, and/or determine a composition of a gas mixture, rapidly and with a sufficiently high degree of accuracy.

Semi-conducting metal-oxide gas sensors attract particular interest for implementation as micro-sensors because they can be built in miniaturized form using techniques known from the field of integrated circuit manufacture.

In recent years semi-conducting metal-oxide type gas sensors having a "micro-hotplate" structure have been developed. FIG. 2(a) is a cross-sectional view which illustrates, schematically, the general structure of a semi-conducting metal-oxide type gas sensor 10 having a micro-hotplate structure. It will be seen from FIG. 2(a) that the base 14 of the sensor 10 has a hollowed-out portion 17 so that the sensing layer 12 is no longer positioned in registration with a thick portion of the base 14. Accordingly, the heater 16 which is used to heat the sensing layer 12 only needs to heat a reduced mass of material (including a relatively thin supporting membrane M), which reduces the power consumed by the gas sensor as well as enabling the temperature of the sensing layer 2 to be increased rapidly (thus reducing the time necessary for making a measurement and reducing the time necessary for cleaning the sensing layer). Moreover, this rapid heating causes less damage to the material forming the sensing layer.

FIGS. 2(b) and 2(c) illustrate sensors having two different types of micro-hotplate architectures.

In the sensor 20 of FIG. 2(b), the sensing layer 22 is formed on an insulating layer 23 which, in its turn, overlies the base 24. Conductors 28 lead out from the measuring electrodes and heater to make contact with electrode pads 29 provided on the base 24. Additional wiring (not shown) connects the electrode pads to further circuitry, notably a source of current for the heater, and circuitry for processing the signals measured by the measurement electrodes. The sensor 20 of FIG. 2(b) has a "closed" type of architecture in which the base 24 has a continuous surface supporting the insulating layer 23.

The sensor 30 illustrated in FIG. 2(c) has a "suspended" type of structure in which the base 34 has a frame-type shape with a central opening 37a and the sensing layer 32 and its insulating layer 33 are suspended over the opening.

Typically, the measurements obtained from a single semi-conducting metal-oxide gas sensor element on its own are insufficient to enable a gas to be identified with a sufficient degree of certainty, because the selectivity of such sensor elements tends to be low. Accordingly, conventionally these sensing elements are used in arrays of multiple sensing elements disposed side-by-side, and each element in the array has a different material forming its sensing layer. The set of measurements obtained from the whole array forms a cloud of data points which can be processed using statistical techniques so as to determine whether or not a given gas is present and/or to determine what is the composition of the gas mixture that has been presented to the array. The set of measurements can be considered to represent a kind of fingerprint that is characteristic of the nature of the gaseous species present in the gas under analysis and their concentrations.

The selectivity and/or the detection-accuracy of an array of semi-conducting metal-oxide gas sensing elements can be improved by increasing the number of data points used in the statistical processing, for example by deriving multiple measurements from each sensing element of the array when it is exposed to a given gas sample. This amounts to obtaining a more detailed fingerprint representative of the gas sample. Various techniques are known for obtaining multiple measurements from each sensing element in an array of semi-conducting metal-oxide gas sensing elements and, in general, they involve changing the operating conditions applicable when the various measurements are taken, for example: by measuring the impedance of each sensor element at more than one operating temperature and/or when different profiles of changing temperatures are applied to the sensing layer, by sampling the sensing layer's impedance at different times during its exposure to the gas sample, by measuring the sensing layer's impedance with or without simultaneous exposure to ultraviolet light, etc.

Although micro-sensors using semi-conducting metal-oxide gas-sensing technology and having a micro-hotplate architecture have been developed, addressing demands for small size and speed of measurement, there is a continuing need to improve the accuracy of the results produced by such micro-sensors.

Other micro-sensors have been developed using chemoresistor technology, notably microsensors using conducting polymers. It is desirable to improve the accuracy of the results produced by these sensors also.

SUMMARY OF THE INVENTION

The preferred embodiments of the present invention provide a chemoresistor type gas sensor having a multi-storey structure which gathers different measurements from usual for a gas sample, enabling gas composition and/or identity to be determined based on a new set of data points.

The preferred embodiments of the present invention provide a chemoresistor type gas sensor having improved performance, notably increased accuracy in detecting target gases and improved accuracy in determining the composition of a gas sample (after an appropriate learning phase).

More particularly, the present invention provides a gas sensor as defined in claim 1 appended hereto, and a method of operating a gas sensor as defined in claim 12 appended hereto.

In the gas sensors according to the present invention, the adoption of a multi-storey architecture provides a new avenue for generating measurements that can be used for the characterization of the gas under analysis. At least one first storey in the gas sensor comprises a semi-conducting metal-oxide or conducting polymer gas sensing element which is exposed to the gas under analysis after that gas has already been in contact with a second storey in the sensor. The second storey carries a layer of material which, when activated, changes the character of the gas sample to which it is exposed. The precise composition of the gas contacting the sensing layer of the first storey can be changed by selectively activating the layer of selectively-activatable material of the second storey. By measuring the response of the gas sensing element of the first storey at times when the selectively-activatable material of the second storey is activated, different data points (measurements) can be gathered compared to the case of using a conventional single-storey architecture consisting of the first storey alone. This provides a new approach for generating the set of data points that can be included in the statistical processing which characterizes the gas undergoing analysis. Accordingly, an additional degree of freedom is provided when designing gas sensors adapted to particular applications.

The multi-storey architecture according to the invention can be exploited not only to generate different measurements compared to those gathered using a conventional single-storey architecture but also to increase the number of measurements that are gathered, thereby improving the accuracy of the results produced by the gas sensor.

Gas sensors embodying the invention can ensure that a satisfactory number of measurements are generated, for use in the process of analysing/characterising the gas sample, by varying operating conditions at times when measurements are taken applying techniques based on those that have been implemented in prior art sensors, notably by taking measurements: at times when the semi-conducting metal-oxide (or conducting polymer) sensing layer and/or the selectively-activatable material layer is held at different temperatures and/or is subjected to different heating profiles, at times when the semi-conducting metal-oxide sensing layer (or conducting polymer) and/or the selectively-activatable material layer is exposed to UV radiation and at times when it is not exposed to such radiation, etc. Moreover, as explained below certain additional, new techniques are made possible by the use of a multi-storey architecture.

In certain preferred embodiments of the invention, two or more chemoresistor type gas-sensing elements are stacked to form a multi-storey structure, and the gas undergoing analysis passes through the different storeys successively, so that the composition of the gas reaching a subsequent storey is influenced by the presence and operation of the gas sensing layer(s) of the preceding storey(s). This stacked structure provides the possibility of producing a rich set of measurements, during exposure of the gas sensor to a gas sample, in a variety of ways including but not limited to:
  a) selecting particular combinations of materials for the sensing layers of the various storeys in the overall gas sensor device,
  b) taking measurements when particular combinations of sensing layers in the stack are activated (and the others deactivated), and
  c) measuring the time difference between the time when a sensing layer at one position in the stack undergoes a particular change in impedance and the time when a sensing layer at a different position in the stack undergoes an associated change in impedance.

The particular combination of materials used in the different sensing layers can be tailored to the particular target application, for example: it can be tailored to the expected composition of the gas that is likely to be encountered, optimized for enabling detection of (or measurement of the concentration of) a specific target gaseous species, etc.

In certain embodiments of the invention the selectively-activatable material of the second storey does not form part of a gas sensing element, that is, there is no measurement transducer associated with this material. In such embodiments it could be considered that the storey bearing the selectively-activatable material is a type of active filter which can be switched on or off, as desired. In such embodiments, various different arrangements are possible for positioning the selectively-activatable material of the second storey relative to the sensing layer of the gas-sensing element first storey. In one possible arrangement a chamber can be defined between the first and second storeys and the selectively-activatable material of the second storey as well as the sensing layer of the first storey can both be located in this chamber, disposed on opposing walls. In another possible arrangement, a membrane/substrate is located in-between the selectively-activatable material of the second storey and a space contacting the sensing layer of the first storey and openings are provided in this membrane/substrate so as to enable gas to pass from the second storey to the first storey.

The selectivity and sensitivity of gas sensors embodying the invention, and more generally of gas sensors of chemoresistor type, can be increased by applying pulsed UV radiation to at least one sensing layer in the sensor (instead of constant UV exposure) and ensuring that the properties of the UV pulses are adapted to the material forming the sensing layer, to the target gas to be detected and to the operating conditions.

In a second aspect, the present invention provides a gas sensor as defined in claim 18 appended hereto, and a method of operating a gas sensor as defined in claim 19 appended hereto.

Measurement data useful to characterise a gas can be obtained by analysis of transient effects that are observable in the response of a gas sensor when the sensor is being exposed to a gas sample and UV illumination is switched on. In a third aspect, the present invention provides a gas sensor as defined in claim 20 appended hereto, and a method of operating a gas sensor as defined in claim 21 appended hereto.

In certain embodiments of the invention it is advantageous to use a micro-hotplate structure to support sensing layers of the gas sensing elements, so as to obtain rapid heating and cleaning of the gas sensing layers.

BRIEF DESCRIPTION OF THE DRAWINGS

The above and other features, advantages and applications of the present invention will become more apparent from the following description of preferred embodiments thereof, given by way of non-limiting examples, and the accompanying drawings, in which:

FIG. 2 shows diagrams illustrating the general structure of semi-conducting metal-oxide gas sensors having a micro-hotplate architecture, in which:

FIG. 8 illustrates a gas sensor having a multi-storey structure including stacked arrays of gas sensing elements;

FIG. 9 illustrates a compact gas micro-sensor device incorporating gas sensing elements arranged in series as in the first preferred embodiment of the invention;

FIGS. 16A and 16B illustrate a new technique for increasing gas sensor sensitivity and selectivity by controlling the time of exposure of a sensing layer to ultraviolet light, in which:

FIG. 16A shows an example of UV pulses suitable for use in the new technique, and FIG. 16B shows a test arrangement used to measure the effect of applied UV pulses;

FIGS. 17A to 17C show experimental results obtained using the test arrangement of FIG. 16B, in which FIG. 17A shows results obtained when a semiconducting metal oxide gas sensor was exposed to air+$H_2S$ without application of UV, with constant exposure to UV, and with exposure to UV pulses of controlled duration, FIG. 17B shows results obtained when a gas sensor was exposed to air+$NH_3$ without application of UV, with constant exposure to UV, and with exposure to UV pulses of controlled duration; and FIG. 17C compares the results obtained in FIGS. 17A and 17B in the case of gas samples at a concentration of 1 part per million;

FIG. 18 illustrates transient effects seen in the response of a sensing layer at onset of exposure to ultraviolet light, in which:

DETAILED DESCRIPTION OF CERTAIN EMBODIMENTS

Certain presently-preferred embodiments of the invention will now be described with reference to FIGS. 3 to 19.

Figure 3:
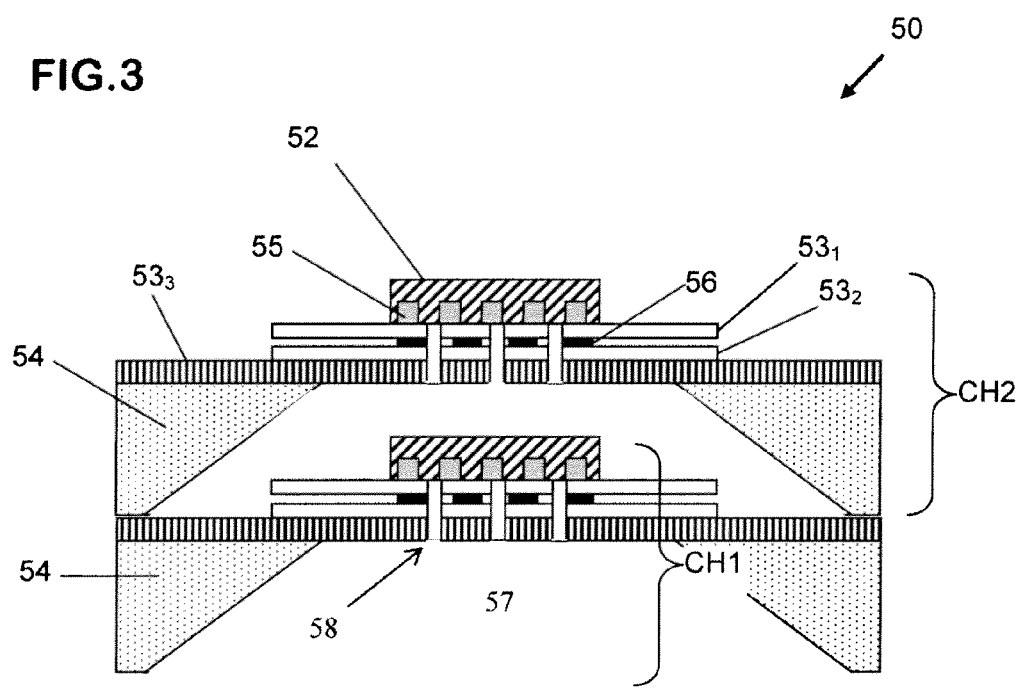
FIG. 3 schematically illustrates the stacking of gas sensing elements of chemoresistor type to form a multi-storey gas sensor according to a first preferred embodiment of the invention.
Figure 4:
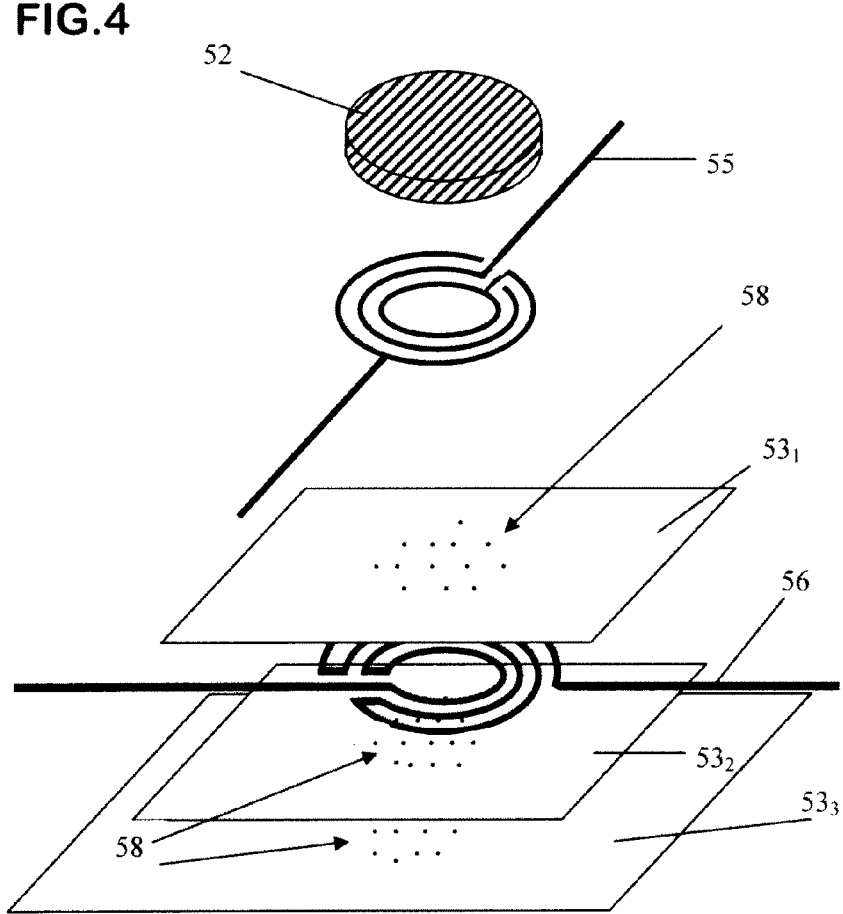
FIG. 4 is an exploded view of a portion of a gas sensing element shown in FIG. 3.
Figure 5:
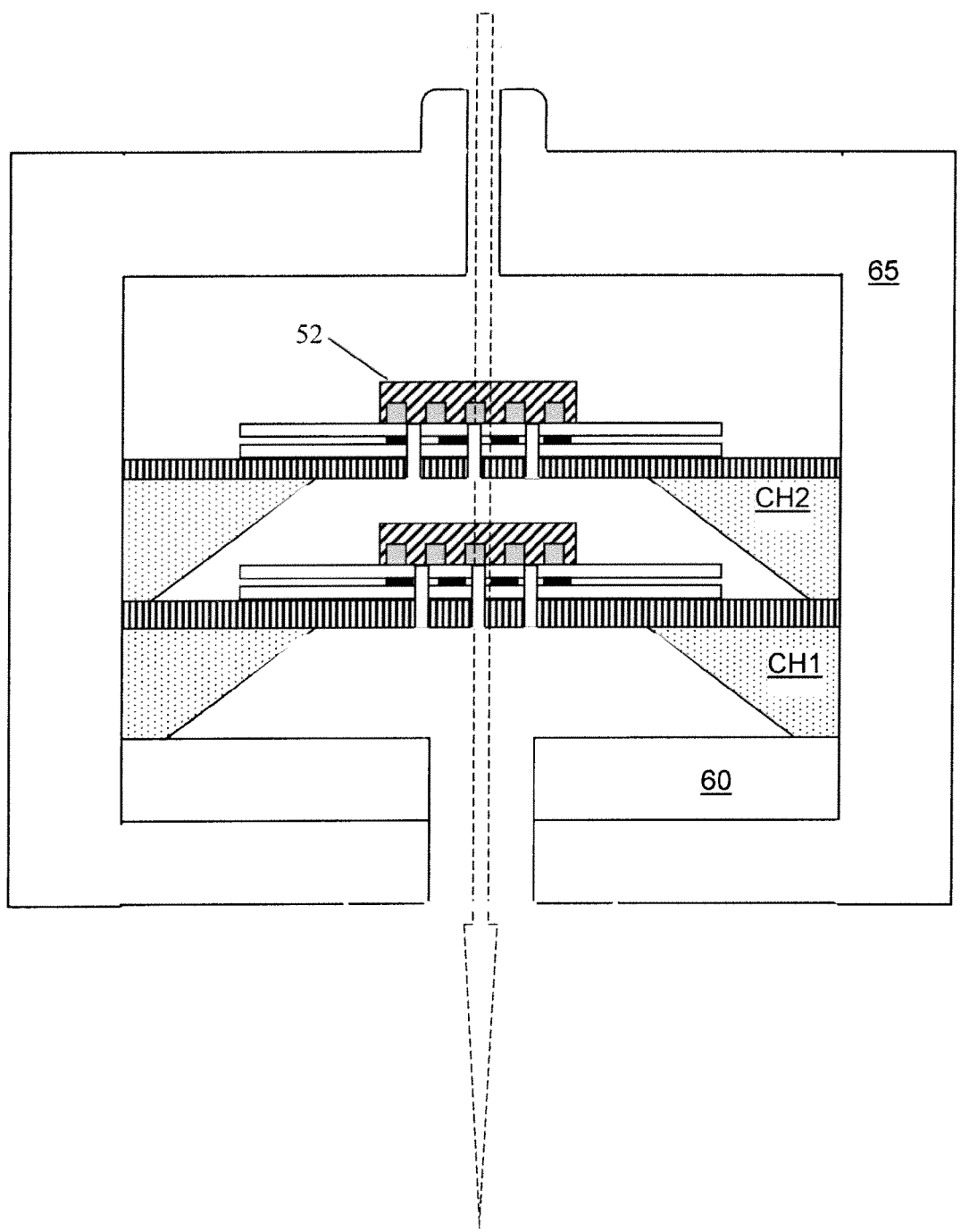
FIG. 5 illustrates a multi-storey gas sensor according to the first preferred embodiment of the invention.

A first, currently-preferred embodiment of the invention is illustrated in FIGS. 3 to 5. According to the first preferred embodiment of the invention a multi-storey chemoresistor type gas sensor is constructed by stacking two (or more) gas sensing elements CH1, CH2 to form a multi-storey structure. FIG. 3 illustrates how the gas-sensing elements CH1, CH2 are arranged relative to one another. FIG. 4 is an exploded perspective view of the structure of each of the gas-sensing elements CH1, CH2 (omitting the base substrate), and FIG. 5 illustrates an overall gas sensor structure that includes the gas-sensing elements CH1, CH2 stacked as illustrated in FIG. 3 and indicates gas flow through the sensor.

FIGS. 3 to 5 illustrate the stacking of two gas sensing elements but it is to be understood that the invention can be implemented also in embodiments in which three or more gas sensing elements are stacked.

As illustrated in FIGS. 3 and 4, each of the sensing elements CH1, CH2 includes a sensing layer 52 made of a semi-conducting metal oxide, supported on a membrane structure 53. The sensing layers may be made of various materials including, but not limited to $SnO_2$, $In_2O_3$, ZnO, $RuO_2$, $WO_3$, and $AB_2O_4$ (spinel type oxides); catalytic materials can also be used (typically mixed with the oxides), such as platinum, rhodium, gold, etc.; and materials can be used which have both sensing and catalytic properties e.g. titanium oxide. Alternatively, if the sensing layer is made of a conducting polymer then it may be made of various materials including, but not limited to, polyaniline, polypyrrole, polythiophene, polyacetylene, poly(phenyl vinlene), and poly(3, 4-ethylene-dioxythiphene), with any desired doping.

The present invention is not particularly limited with respect to the techniques used for deposition of the sensing material (and any catalytic material). As is well-known, the nature of the surface of the deposited sensing/catalytic material influences the efficiency of the sensor; nano-particles, and porous surfaces produced by physical vapour deposition (PVD), yield good efficiency. In general, the deposition technique will be adapted to the particular material being deposited, bearing in mind efficiency considerations. The thickness of the layer 52 will vary depending on the deposition technique and, typically, will be 100-1000 nm when PVD is used, and 10-100 μm otherwise (although these values can be varied).

In the example illustrated in FIGS. 3 and 4 the membrane structure consists of three thin layers $53_1$, $53_2$, $53_3$ of insulating material (for example $SiO_2$, or $Si_3N_4$, or $SiO_xN_y$, or $SiN_x$). The thin layers $53_1$, $53_2$ sandwich a heater (described below), and serve to insulate this heater from other components. The layer $53_3$ functions as a membrane to support the overlying layers. Stresses in this multi-layer membrane structure can be reduced by forming the layers from different materials. In this example, layer $53_1$ is made of $SiO_2$, layer $53_2$ is made of $SiN_x$ and layer $53_3$ is made of $SiO_2$.

Figure 1:
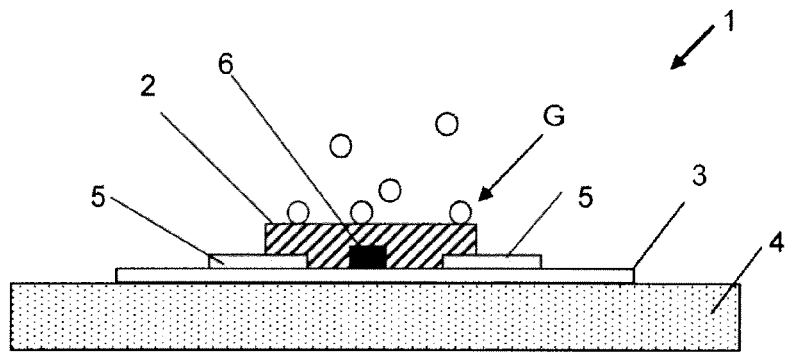
FIG. 1 is a diagram indicating schematically, in cross-section, the general structure of a semi-conducting metal-oxide gas sensor.
Figure 2A:
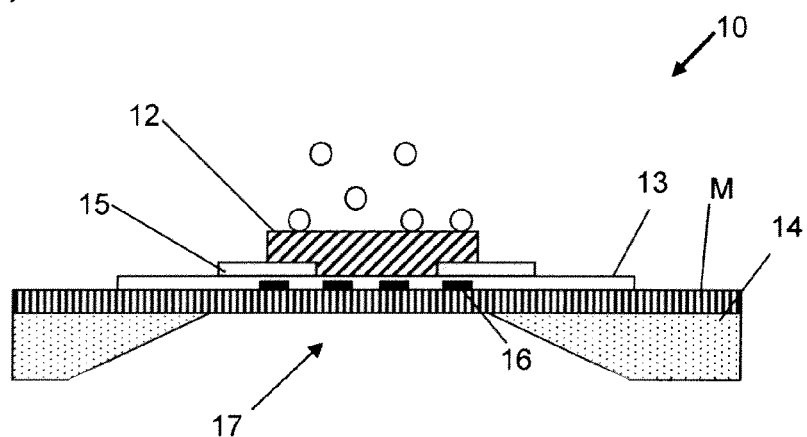
FIG. 2(a) is a cross-sectional view illustrating the overall structure of a micro-hotplate type architecture.
Figure 2B:
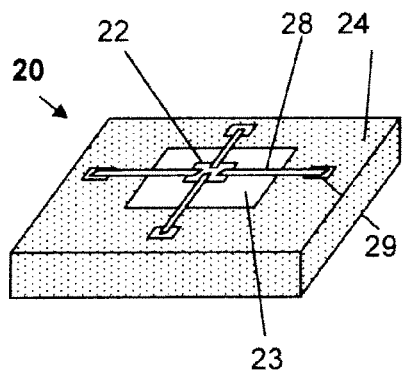
FIG. 2(b) illustrates a "closed" type of micro-hotplate architecture.
Figure 2C:
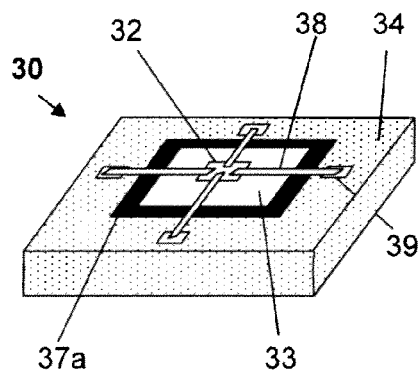
FIG. 2(c) illustrates a "suspended" type of micro-hotplate architecture.

The membrane structure 53 is mounted on a base substrate 54 which is relatively thick at the edges but has a recess 57 so as to provide a micro-hotplate structure. In the example shown in FIG. 3 the recess 57 takes the form of an opening through the base substrate. However, the micro-hotplate structure is still of the "closed" type illustrated in FIG. 2(a) because the membrane structure 53 covers the opening in the base substrate 54. Typically the base substrate 54 is made from a silicon wafer because Si wafers can be machined with high precision using standard semiconductor manufacturing processes.

As illustrated in FIG. 3, holes 58 are provided through the membrane structure 53. Alternatively, the layers making up the membrane structure 53 may be porous. In this example the holes/pores 58 have a diameter of 10 μm, but the invention is not limited to this value.

Because the gas-sensing elements CH1, CH2 have a closed type of micro-hotplate structure, and because holes 58 (or pores) are provided in registration with the sensing layers 52, gas passing through the gas sensor 50 traverses each sensing layer 52, maximising the contact that each sensing layer 52 has with the gas sample. Firstly, this tends to maximise any effect that the gas produces on the electrical properties of this sensing layer 52 and, secondly, this tends to increase changes in the gas that flows to the subsequent storey.

As indicated in the previous paragraph it is advantageous to locate the holes 58 in the active area of the sensor (i.e. in registration with the sensing layer 52). However, the position of the holes 58 can be varied. If all the holes 58 are outside the active area then the gas passing to the subsequent storey will undergo less modification during its passage through the current storey, but it will still be possible to measure the time taken for the gas to diffuse from this storey to the next.

In each of the sensing elements CH1, CH2, measurement electrodes 55 are provided in contact with the respective sensing layer 52 so as to detect changes in the electrical properties of the sensing layer when it is exposed to a gas. The particular changes that take place depend on the nature of the material forming the semi-conducting metal oxide and on the gaseous species present in the gas sample but, in general, consist of oxidation and/or reduction reactions changing the impedance of the sensing layer. As indicated above, in general it is necessary to heat the sensing layer in order for appreciable adsorption (and oxidation/reduction) to take place.

Accordingly a heater 56 is provided in-between the insulating layers $53_1$, $53_2$. The heater itself can also be used as a temperature sensor monitoring a change of the resistance. Although not shown in the figures, each gas sensing element CH1, CH2 also includes a different temperature sensor so as to be able to monitor the temperature attained by the sensing layer 52.

In this example the measurement electrodes are made of Pt, with an underlying Ti adhesion layer, and take the form of two interlocked conductor elements having portions taking a generally circular shape (as shown in FIG. 4). In practice the measurement electrodes 55 have a greater number of interlocking circular portions than represented in FIG. 4. In this example each measurement electrode is 0.2 μm thick and 10 μm wide, and the measurement electrodes are spaced apart from one another by 10 μm. The precise positioning and shape of the measurement electrodes 55 can be varied. However, in this example the measurement electrodes 55 are positioned and shaped so as to be well-located for detecting the expected change in electrical properties of the sensing layer 52.

In a similar way, in this example the heater 56 takes the form of a generally circular element which underlies the sensing layer 52. In this example the heater 56 is made of Ti/Pt like the measurement electrodes, but in the case of the heater 56 the Ti/Pt forms a heater pattern including conductive traces which bend back on themselves to form a series of nested loops. Typically the conductive traces of the heater pattern are 0.2 μm thick and 20 μm wide. Materials other than Ti/Pt, for example multilayers of refractory conductors (Mo, Ta, W, . . . ), but also polysilicon, may be used for the heater 56.

The precise positioning of the heater 56 and temperature sensor can be varied. However, the transfer of heat from the heater 56 to the sensing layer 52 is particularly efficient when the heater is provided in registration with the position of the sensing layer, and shaped, as shown in FIGS. 3 and 4. In this example the heater 56 is separated from the sensing layer 52 by the membrane $53_1$ so as to ensure electric isolation of the heater 56 from the measurement electrodes 55.

In one example using measurement electrodes 55 and a heater 56 having the configuration illustrated in FIG. 4, the insulating layers $53_1$, $53_2$ are about 0.5 μm thick layers of $SiO_2$ and SiNx, the other insulator layer $53_3$ is about 0.8 μm thick $SiO_2$ layer and the substrate 54 is a silicon wafer of 300~500 μm thick at the edges. In this example, a sensing layer 52 made of ZnO can be brought up to a temperature of 500° C. very rapidly (notably in 30 milliseconds).

Any convenient techniques can be used for fabricating the sensing elements CH1, CH2.

As shown in FIG. 3, the sensing elements CH1, CH2 are stacked relative to one another. In general, the sensing layer 52 is porous because it has a grain-based structure or is made of nano-particles, nano-rods, nano-wires or nano-tubes. In preferred embodiments of the invention the sensing layer 52 has a nano-particle structure because the ratio of surface area to volume is high for such a structure, providing a large surface area on which chemical reactions can occur with the gas under test. When the sensing layer 52 of the sensing element CH1 (or of the sensing element CH2) is exposed to a gas sample the gas will penetrate into and through the sensing layer 52 because the sensing layer is porous.

In the first preferred embodiment of the invention, the layers $53_1$, $53_2$, and $53_3$ are traversed by holes 58 so that the gas penetrating the sensing layer 52 passes all the way through the relevant gas sensing element. Accordingly, gas will pass through the sensing layer 52 of one sensing element (say CH2) before reaching the sensing layer 52 of the subsequent gas-sensing element (say CH1). The holes 58 may be made by standard processes used in semiconductor manufacture (for example using photolithography and reactive ion etching, etc.) In a variant structure the underlying layers $53_1$, $53_2$, and $53_3$ are porous and it is then not necessary to provide the holes 58. Incidentally, in a case where the recess 57 is spanned by a thin portion of the substrate 54, underlying the membrane structure 53, holes 58 can be provided in that substrate portion also, or it can be made of a porous material.

The gas passing through one of the gas-sensing elements (e.g. CH2) is modified, notably dependent on the type of oxide or conducting polymer used in the sensing layer, the temperature of the sensing layer, effects of exposure to UV radiation (if any) and the time-profile of the temperature that is applied to the sensing layer. Accordingly, the signal measured by the measurement electrodes 55 of a subsequent gas-sensing element (e.g. CH1) depend not only on the nature of the oxide or conducting polymer in the sensing layer of this gas sensing element CH1, and its operating conditions (temperature, exposure to any UV radiation, time-variation in applied temperature, frequency of the voltage, etc.) but also on the nature of the oxide or conducting polymer in the gas-sensing element of the preceding storey and its operating conditions.

FIG. 5 illustrates the overall structure of a gas sensor based on the stacked sensors of FIG. 3. The gas flow through this sensor is illustrated using an arrow marked using dashed lines. As shown in FIG. 5 the gas-sensing elements CH1, CH2 are stacked on a base 60 inside a housing 65 having an inlet (for receiving gas to be analysed) and an outlet. The base 60 may be made, for example, of glass and the housing 65 made of PTFE, although the invention is not limited to these materials. Depending on the number of gas sensing elements to be traversed by the gas sample under analysis, it may be necessary or desired to use a pump or the like to force gas circulation through the gas sensor. However, as explained below, a useful measurement can be produced by allowing the gas sample to simply diffuse through the gas sensor. It is believed that simple diffusion, without forced circulation, should be sufficient to achieve satisfactory measurements in an acceptable time frame in a gas sensor employing two or three stacked gas-sensing elements.

According to the first preferred embodiment of the invention, gas-sensing elements can be stacked in numerous different configurations. A few of the possible configurations are illustrated in FIGS. 6 to 11.

Figure 6:
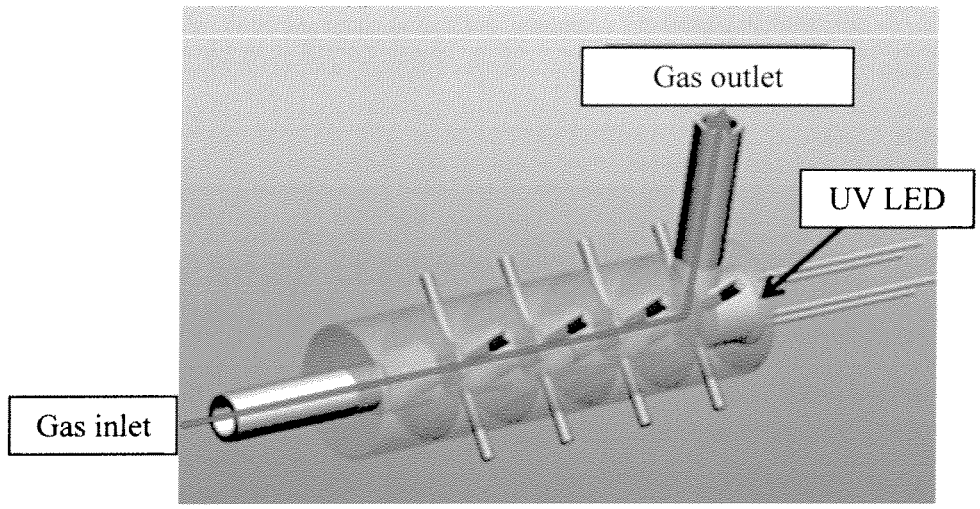
FIG. 6 illustrates a first approach to mounting gas sensing elements in series as in the first embodiment of the invention.

FIG. 6 shows a configuration in which four gas-sensing elements are arranged in series (stacked) between a gas inlet and a gas outlet, and a light-emitting diode is provided in the housing so as to be able to illuminate the gas-sensing elements with ultraviolet light. Leads can be seen passing through the side wall of the housing for connecting the heaters and measurement electrodes of the various gas-sensing elements to external circuitry (and, in practice, additional leads could be provided, if required, for temperature sensors).

In the FIG. 6 configuration, the LED may be arranged to illuminate all of the sensing elements in the housing, notably by supporting the sensing layers of the various storeys on membranes/insulating layers that allow UV to pass (e.g. very thin layers, notably layers up to around 2 μm thick). Alternatively, if it is desired to illuminate some, but not all, of the sensors with UV light then UV barrier layers may be provided at appropriate locations in the housing.

Figure 7:
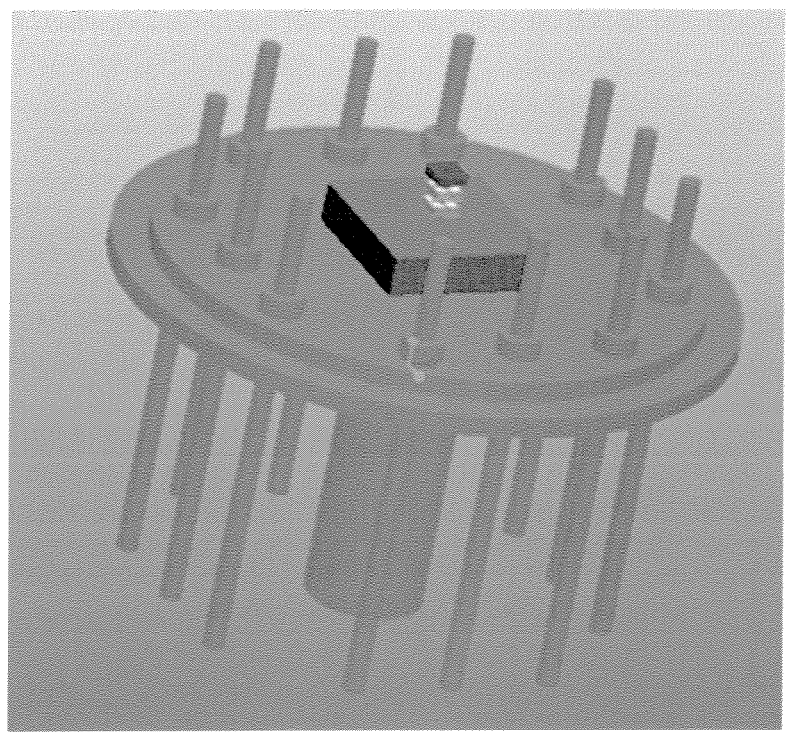
FIG. 7 illustrates a second approach to mounting gas sensor elements in series as in the first embodiment of the invention.

FIG. 7 illustrates two stacked gas-sensing elements, and a gas connector, mounted on a standard TO5 type support for connect-and-plug semiconductor devices.

FIG. 8 illustrates a multi-storey architecture in which arrays of gas-sensing elements are stacked. In this example one 2×2 array of semi-conducting metal-oxide gas sensors is stacked on another 2×2 array. However, it is to be understood that the invention is not limited with regard to the dimensions of the stacked arrays nor with respect to the number of arrays included in the stack. Moreover, it is not excluded to vary the dimensions of the arrays from one storey to the next.

FIG. 9 illustrates a compact device incorporating a gas sensor according to the first embodiment of the invention as well as circuitry to drive the gas-sensing elements and process their output. This compact device takes the form of a capsule roughly 1 cm by 2.5 cm in size yet including multiple gas-sensing elements (notably, two to seven stacked gas-sensing elements).

Figure 10:
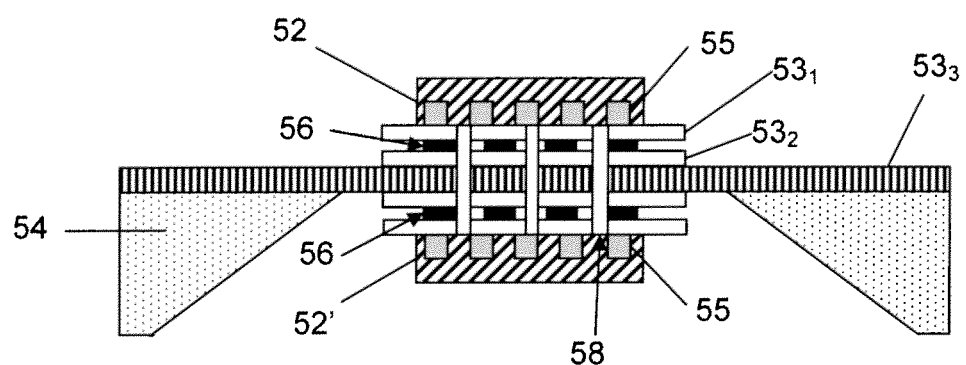
FIG. 10 illustrates a multi-storey gas sensor in which two gas sensing elements are mounted in series in a back-to-back arrangement on a single substrate.

FIG. 10 illustrates a device in which two gas sensing elements are mounted n series using a single supporting substrate 54. It is advantageous to use different materials for the sensing layers 52, 52' of the two gas sensing elements.

Figure 11:
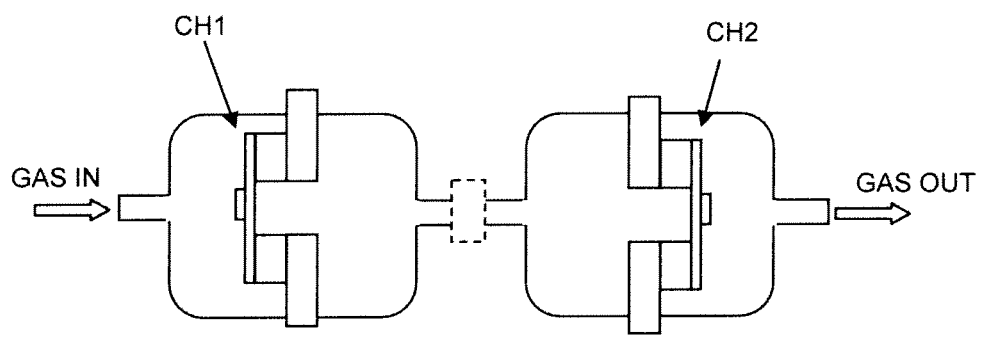
FIG. 11 illustrates a multi-storey gas sensor in which successive gas sensing elements are spaced from each other.

FIG. 11 illustrates a gas sensor device in which the series-connected gas sensing elements of the multi-storey structure are spaced from each other, possibly with intervening elements (indicated by the box in dashed lines in FIG. 11). This architecture differs from known devices (containing a series of chambers through which gas passes, with different sensors in each chamber), by virtue of the fact that the gas passing through the device is obliged to pass through the sensing layer/membrane of the upstream gas sensing element CH1 before reaching the downstream gas sensing element CH2 and, thus, the gas is modified before it reaches the downstream sensing element.

Although FIG. 11 shows the second gas sensing element CH2 oriented in a mirror-image orientation relative to the first gas sensing element CH1, it will be understood that both elements may be arranged in the same orientation in the gas flow path. Moreover, it will be understood that three or more gas sensing elements may be interconnected in the manner shown in FIG. 11.

Although not shown in FIG. 3 to 8, 10 or 11, the measurement electrodes 55, heaters 56 and temperature sensors in the gas sensors according to the first preferred embodiment of the invention all are connected to (or are adapted for connection to) other circuitry, notably for supplying current and taking measurements using well-known techniques that do not require description here.

It is worthwhile to mention the following features specific to the present invention.

a) How to Arrange Various Sensing Materials "Vertically" (i.e. in the Various Storeys)

In general, the number and choice of materials, as well as their relative positioning on the different storeys of a multi-storey device according to the invention is designed so as to increase the discriminant ability of the overall sensor device in a manner dependent on the specific target application. Numerous configurations will readily occur to the skilled person based on his common general knowledge, notably in view of the reactivities of different gases with different semiconductor metal oxide and conducting polymer materials. For the purposes of illustration, an example is discussed below regarding how discrimination of a target gas in the presence of an interference gas can be made easier by virtue of the choice of a combination of materials to use in the sensing layers of the different storeys in a multi-storey sensor according to the invention.

All gases have different reactivities with conducting polymers and metal oxide gas sensing materials such as ZnO, $SnO2$, $In_2O_3$, and so on. It is very difficult to discriminate a gas which has lower reactivity with a specific material when the target gas is in an interference gas which has higher reactivity. For example, to distinguish $NH_3$ is very difficult in an $H_2S$ atmosphere because $H_2S$ is more reactive in comparison with $NH_3$. According to previous research, the bond energy of H—SH is 381 KJ/mol, and the bond energy of H—$NH_2$ is 450 KJ/mol. Additionally, two $NH_3$ molecules release three free electrons through a reaction with adsorbed oxygen on the surface of ZnO. On the other hand, one $H_2S$ molecule releases three free electrons through the reaction. As a result, $H_2S$ is more reactive than $NH_3$ with a ZnO sensing material. However, as described below, $NH_3$ is selectively detectable using a multi-storey architecture according to the invention.

For example, suppose that there are two kinds of sensing material. One, Material A, shows about 90% reactivity and 10% reactivity for $H_2S$ and $NH_3$, individually. And the other, Material B, shows about 60% reactivity and 40% reactivity for $H_2S$ and $NH_3$, individually. The expression "reactivity" mentioned here denotes a parameter quantifying how many molecules can decompose into inactive gases on the surface of metal oxide sensing materials. For example, $NH_3$ can decompose into $H_2O$ and $N_2$ on the surface of ZnO and $H_2S$ can decompose into $H_2O$ and $SO_2$ on the surface. It is impossible to generate a larger measurement signal for $NH_3$ using these two materials, A and B, in an $H_2S$ atmosphere. However, it is possible to generate a larger measurement signal for $NH_3$ if the sensing materials are arranged vertically, that is, in subsequent storeys of a multi-storey architecture according to the invention.

Suppose that material A forms the sensing layer in the top storey, through which gas enters, and material B forms the sensing layer in the bottom storey that receives gas after passage through the top storey. In this case, gas can get to the surface of material B only through material A. Suppose that 1000 molecules each of $NH_3$ and $H_2S$ pass through the materials. While the $1000H_2S$ molecules pass through Material A, 900 of the molecules decompose into $H_2O$ and $SO_2$. On the other hand, in the case of $NH_3$ under the same conditions, only 100 molecules decompose into $H_2O$ and $N_2$. This means that a greater number of $NH_3$ molecules can reach and react with Material B in comparison with the number of $H_2S$ molecules. In the above example, $900NH_3$ molecules can get to Material B, but only $100H_2S$ molecules can get to Material B. Accordingly, the measurement signal of $NH_3$ increases relatively in comparison with the signal of $H_2S$. This is a basic example of how materials may be selected to ensure that the gas sensor device has good selectivity for a gas which has lower reactivity than an interference gas. As mentioned above, there can be various combinations for the sensing materials and their relative disposition depending on the specific application.

b) How to Use Selective Activation of Various Sensors of the Multi-Storey Architecture.

One of the advantages of the multi-storey architecture provided by the invention is that this architecture makes it possible to make use (for gas discrimination) of the difference of gas diffusivity through sensors which are arranged in series. The diffusivity through each storey is dependent on the sensing-layer material itself and its operating temperature. So, it is important what kinds of materials are used and also important what is the operating temperature. This means that the operating sequence is very important to control the diffusivity. The multi-storey architecture can be used with various operating sequences on the temperature. To remove an interference gas for target gases, operating temperature should be well controlled. But a profile of the sequence can be determined experimentally for a specific application.

c) Measurement of Time Difference Between Reactions of Successive Sensing Elements:

In an embodiment including at least two stacked gas sensing elements, one of the additional techniques that can be implemented for increasing the size of the cloud of data points to be analysed, and which derives from the use of a multi-storey architecture, consists in measuring the time difference between a moment when the sensing layer of one storey in the architecture reacts to the gas undergoing analysis and a moment when the sensing layer in a subsequent storey (e.g. the next storey in the direction of gas flow) has a comparable reaction to the gas. When the flow of gas is not being forced, this time difference can be characteristic of the rate of diffusion of the gas through the sensing layer of the "one" storey and, in view of the fact that rates of diffusion of various gaseous species through different materials are known, can serve as an additional parameter helping to identify a gas in the sample undergoing analysis.

The waveforms produced by the measurement electrodes have various characteristic points, for example points where the gradient changes sharply. The particular characteristic point that is best suited to serve as the reference for measuring the above-described time difference tends to vary depending on the particular application. In one example, a time $t1$ is measured corresponding to the moment when an inflection point first appears in the signal output by the measuring electrodes of an upper storey that is first in the gas flow path (this moment corresponding to the onset of a reaction between the sensing layer of this storey and the gas undergoing analysis) and a time $t2$ is measured corresponding to the moment when a corresponding inflection point first appears in the signal output by the measuring electrodes of the subsequent storey in the gas flow path (this moment corresponding to the onset of a reaction between the sensing layer of this subsequent storey and the gas undergoing analysis). The time difference $t2-t1$ is characteristic of the membrane and of the gas and, notably, is influenced by the sensing material 52 in at least the earlier storey in the gas flow path, the size of holes/pores in the layers $53_1$-$53_3$ and the distance between the two sensing layers. The gas can be identified using Fick's Law and known values of diffusion coefficients for different gases.

In a case where the gas under analysis includes more than one species the response of the measurement electrodes will often include respective different features (notably, different points of inflection) that are characteristic of the sensing layer's reaction to these different gaseous species. Accordingly, in this case data can be generated for each gaseous species by measuring the time interval between the corresponding feature in the response of the measurement electrodes of one storey and the equivalent feature in the response of the measurement electrodes of the subsequent storey.

d) How to Produce a Rich Set of Data Points

The first embodiment of the invention enables a rich set of data points to be generated rapidly using a small structure. The number and variety of data points in the set of measurements used for characterizing a gas may be enhanced in a variety of ways, notably:

by increasing the number of gas-sensing elements,
by increasing the number of different materials forming the sensing layers,
by varying the operating conditions applicable to the various sensing layers notably: the operating temperatures, exposure/non-exposure to UV light, applying different time-varying profiles of the operating temperatures (notably applying a profile which involves short intervals at different temperatures and measuring the short-term reactions of the sensing layer), applying a pulsed potential difference to the measuring electrodes and varying the pulse frequency, etc.)

The present invention is not particularly limited with regard to the implementation of a process for generating data points by varying the operating conditions of the various sensing layers in a multi-storey device according to the invention. Different choices can be made regarding: whether to alter the operating conditions of a single sensor, or multiple sensors, at the same time; whether to measure output signals from all sensors, or a sub-set of the sensors, when operating conditions of particular sensors are varied; whether to take discrete measurements (e.g. one or more sets of discrete measurements for each configuration of the operating conditions applied to the set of sensors) or continuous measurements as the operating conditions are varied, etc. For example, plural data points may be generated by simultaneously applying different temperature profiles to each of the sensors in the device and measuring the outputs from the measurement electrodes of all storeys. In general, the different operating conditions applied to the various sensing layers can be tailored to the specific application, in order to optimize the discrimination performance of the device.

A further measurement can be generated in embodiments of the present invention by paying attention to the energy that is needed to maintain the sensing layer (or the selectively-activatable material) at a particular temperature. More particularly, some of the reactions that occur when a gas contacts the sensing layer (or the selectively-activatable material) may be endothermic whereas others may be exothermic. The heat changes during such reactions alter the amount of energy that is needed by the heater in order to keep the relevant sensing layer (or selectively-activatable material) at the nominal operating temperature. This alteration can be detected and used as an additional indication of the properties of the gas sample being analysed. Moreover, this technique can be applied in the second embodiment of the invention described below.

Various interesting new techniques based on the use of pulsed UV light can be applied in order to increase the sensitivity and selectivity of the above-described gas sensors and, indeed, to increase the sensitivity and selectivity of chemoresistor gas sensors in general (i.e. even without using a multi-storey architecture). These new techniques will now be described with reference to FIGS. 16-18.

It has already been proposed to expose semiconducting metal oxide gas sensors to ultraviolet light continuously during a period when measurements are being taken. Further, it has been proposed to apply the UV light in pulses, in order to reduce energy consumption. However, the present inventors have discovered that the sensitivity and selectivity of a semiconducting metal-oxide gas sensor in relation to different gases can be increased dramatically by applying pulsed UV, not continuous UV, and by tailoring the pulse properties to the specific gases, taking into account the operating temperature and the nature of the sensing material. It is believed that this phenomenon arises for the reasons explained below.

Gas molecules have different structures and different binding energies for the various bonds in those molecules. For example, in a molecule of $H_2S$, the bond energy of the H—SH bond is 381 kJ/mol, and in a molecule of $NH_3$ the bond energy of H—$NH_2$ is 450 kJ/mol. When pulses of UV light are applied to a semiconducting metal oxide sensor during exposure to a gas, the duration of the pulses required to activate the molecules varies with the gas species. For a given gas there appears to be an optimal duration of UV illumination in order to maximise the effect that can be observed in the response of the sensing material as detected via the measurement electrodes.

Experiments were conducted using a single semiconducting metal oxide gas sensor having a ZnO sensing layer. Effectively, the specific characteristic of metal oxides such as ZnO, which is photosensitive, is employed. The sensor was exposed in turn to a test atmosphere consisting of clean dry air (relative humidity 0%), and to a gaseous atmosphere containing varying amounts of $H_2S$, under different conditions. In each case the sensing material was exposed to a continuous flow of gas through the sensor at a rate of 200 cm$^3$ per minute.

Figure 16A:
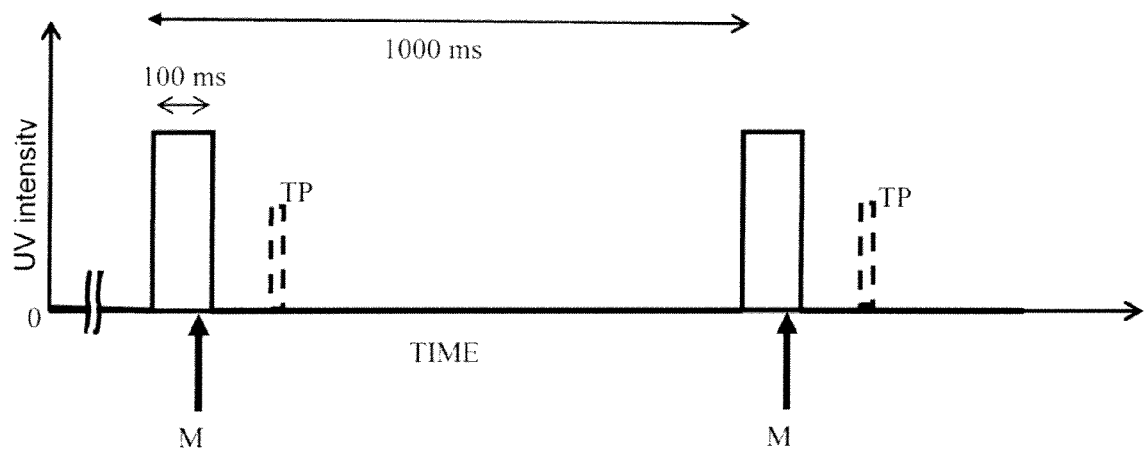

In a first set of experiments the ZnO layer was exposed to pulses of UV light of wavelength 385 nm having the general form illustrated in FIG. 16A while being exposed to the test gases. In each case the response of the ZnO sensing layer was measured 90 ms after the start of each UV pulse (as indicated by the arrows M in FIG. 16A). In a second set of experiments the ZnO layer was exposed to continuous UV illumination at the same 385 nm wavelength while being exposed to the same set of test gases. The experiments were repeated a third time, without UV exposure.

The wavelength of the UV pulses was set at 385 nm in view of the band gap in ZnO. The energy necessary for a charge carrier to cross the band gap in ZnO is 3.3 eV at 25° C., which corresponds to a UV wavelength of 376 nm. Based on theoretical calculations it would be expected that UV wavelengths of 376 nm or below should be used for the UV pulses in order to supply sufficient energy for crossing of the band gap in ZnO; and, indeed, successful experiments were performed using UV pulses having a wavelength of 365 nm. However, in practice, it was found that useful effects were still produced using UV pulses at 385 nm. In general, it is advantageous to set the wavelength of the applied UV pulses based on the energy necessary to cross the band gap in the sensing material in question.

During the tests involving pulsed UV, 100 msec after the end of each UV pulse there was a 20 msec period of heating the ZnO sensing material to 530° C. (indicated in FIG. 16A by the dashed pulses TP). Comparable 20 msec heating periods were applied at comparable times during the tests involving continuous UV and no UV. These short bursts of heating improve the return of the measurement signal to its baseline value.

Figure 16B:
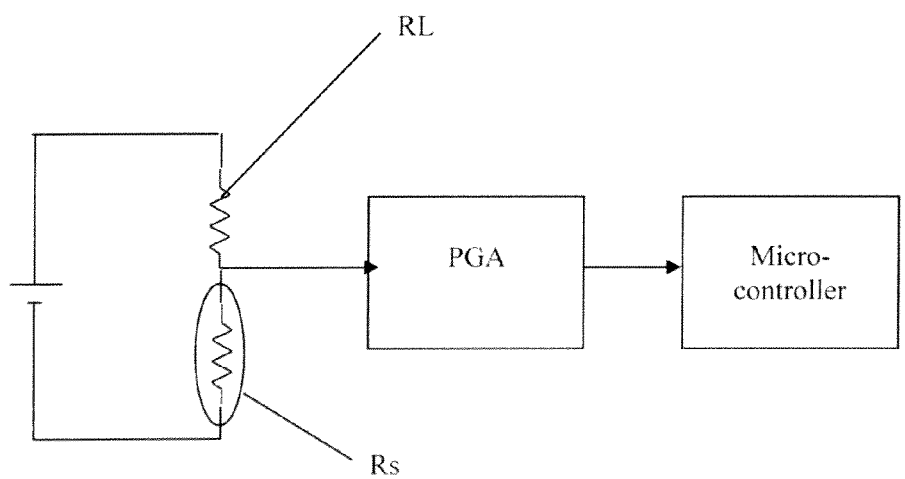

In these experiments, the response of the ZnO sensing layer was measured using a resistance divider structure as illustrated in FIG. 16B. The resistance Rs illustrated in FIG. 16B represents the resistance of the sensing layer ZnO, the resistance RL represents a reference resistor which was connected in series with the ZnO sensing layer. In these experiments, RL was 2.74 MOhms, and the illustrated d.c. power supply provided a voltage of 3.3 volts. The voltage at a point between the ZnO sensing layer and the reference resistor RL was supplied to a programmable gain amplifier which, in turn, supplied the amplified signal to a microcontroller, and measured once per minute. The average of the last four measurements was calculated, to represent the response of the ZnO sensing layer, and the response was monitored over a 20 minute time period.

Incidentally, it will be understood that FIG. 16B is just one example of a measurement circuit that may be used to evaluate the resistance of the sensing layer. Various modifications may be made in the circuit of FIG. 16B (e.g. the output from the amplifier could be supplied to a low pass filter and then to an analog-to-digital convertor), or indeed other circuit arrangements could be used.

The sensitivity of the sensor to $H_2S$ was quantified by evaluating a parameter Ra/Rg where Ra is the resistance of the ZnO sensing material during the exposure to dry air and Rg is the same resistance but during exposure to the atmosphere containing $H_2S$. The experiments were performed using different gas samples containing $H_2S$ at concentrations of 0.1 part per million (ppm), 0.5 ppm and 1.0 ppm, respectively. The results are shown in FIG. 17A.

Figure 17A:
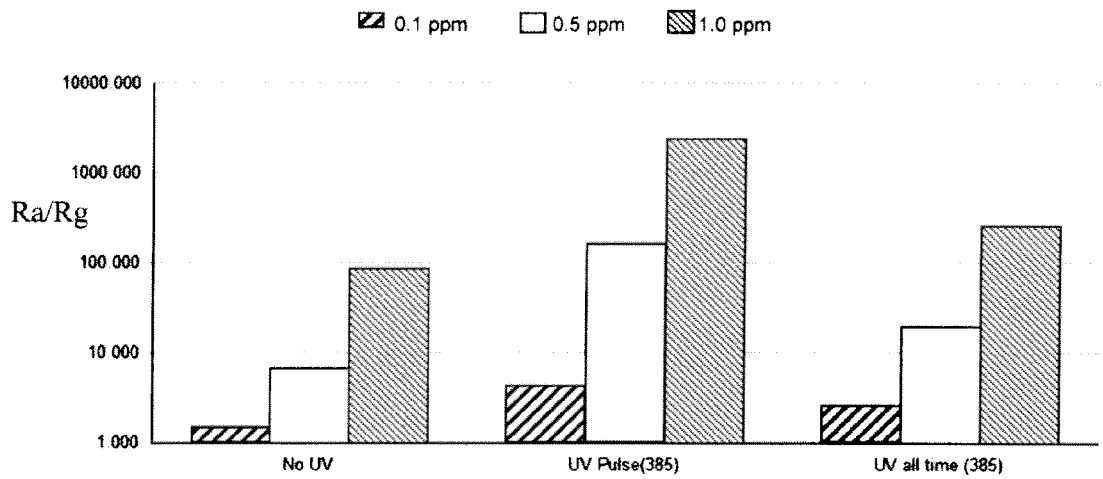

As can be seen from FIG. 17A, the sensitivity of the gas sensor to $H_2S$ is lowest when there is no exposure to UV light, the sensitivity improves somewhat (perhaps twofold) when the measurement is taken during continuous exposure to UV, but there is a large improvement in sensitivity—roughly 5 to 17 times—when the sensor is illuminated using the UV pulses of FIG. 16A having a duration of 100 ms and a duty cycle of 10%.

The above experiments were repeated using a gaseous atmosphere of air with varying amounts of $NH_3$ (using $NH_3$ concentrations of 1, 5 and 10 ppm) but otherwise leaving the conditions unchanged. The results are shown in FIG. 17B.

Figure 17B:
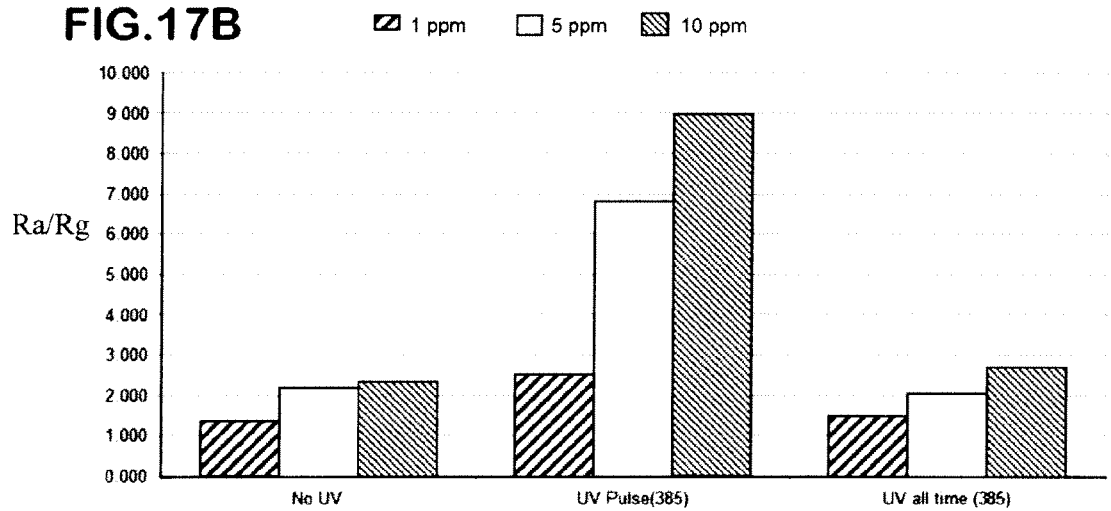

As can be seen from FIG. 17B, the sensitivity of the gas sensor to $NH_3$ is increased when the sensor is illuminated using the UV pulses of FIG. 16A. However, the increase in sensitivity of the gas sensor to $H_2S$ when the UV pulses are applied is significantly greater than the sensitivity increase that is obtained in the case of $NH_3$.

Figure 17C:
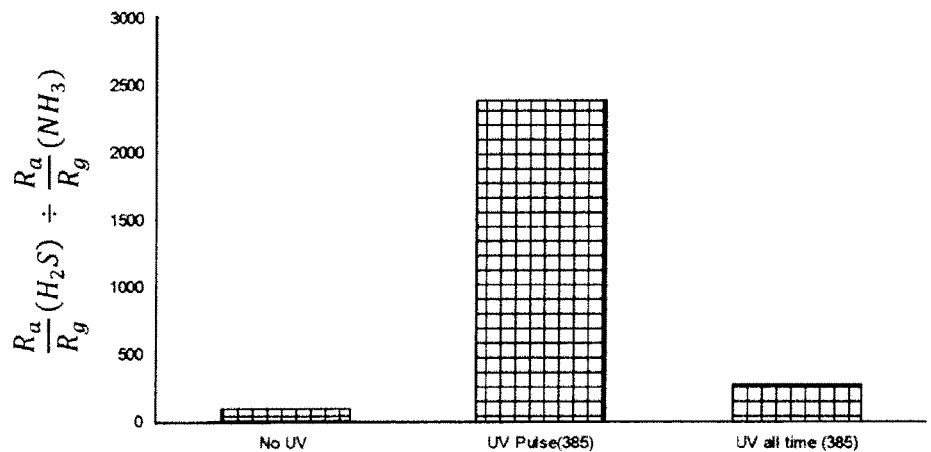

FIG. 17C illustrates the relationship between the increase in sensitivity that was observed for gas samples containing $H_2S$ at a concentration of 1.0 part per million (ppm) and that observed for gas samples containing $NH_3$ at a concentration 1.0 ppm. It can be seen that the sensitivity increase observed for $H_2S$ is of the order of 1000 times the sensitivity increase observed for $NH_3$. The skilled person will readily appreciate that the selectivity of the gas sensor for $H_2S$ (i.e. its responsiveness preferentially to $H_2S$ compared to other gases) is dramatically increased by applying the UV pulses.

It is considered that application of UV pulses of selected wavelength whose duration is suitably set dependent on a target gas (and, advantageously, also set taking into operating conditions) will produce an improvement in gas-sensor sensitivity even when gaseous species different from $H_2S$ and $NH_3$ are being detected and when the sensing material is different from ZnO, provided that the activation energy of the target gaseous species in respect to the chosen sensing material at the selected operating temperature is in a range suitable to be provided by pulses at UV wavelengths. Suitable sensing materials include other semiconducting metal oxide materials (e.g. $TiO_2$, or $SnO_2$ at high temperature, etc.) and semiconducting chalcogenides (e.g. CdS, ZnS, etc.), as well as selected conducting polymers. The optimal duration and/or duty cycle of the UV pulses depends on the target gaseous species, as well as on the selected sensing material, on the wavelength of the applied UV pulses and on the operating temperature.

This technique of applying specifically-designed UV pulses to improve gas sensor sensitivity and selectivity can be employed so as to enable a particular gas sensor to be used to discriminate plural gases. More particularly, a gas sensor can be provided with a control module configured to set the duration and/or duty cycle of UV pulses applied to a sensing layer in the gas sensor to different values each suitable to increase the sensitivity of the sensing layer to a respective different gaseous species (the appropriate value for the duty cycle and operating temperature being determined by experiment, taking into account the target gaseous species, as well as the selected sensing material and the UV pulse wavelength chosen for the selected sensing material).

Alternatively, or additionally, a gas sensor can be provided with a control module configured to apply a measurement protocol adapted to enhance the selectivity of the gas sensor to a target gas. More particularly, the measurement protocol may involve taking measurements first without applied UV and then with applied UV pulses of predetermined wavelength and duty ratio (the duty ratio and operating temperature being set—based on the results of prior testing for the selected sensing material/UV wavelength—to produce a significant increase in sensitivity towards the target gas compared to the increase in sensitivity expected for other likely gas species in the samples). A comparative analysis of the sensor responses observed in the two sets of measurements can be used for detection of the target gas species. Typically, chemometric methods are used to analyse the sensor responses but the invention is not particularly limited with regard to the comparative analysis methods that may be applied.

As mentioned above, the technique according to the second aspect of the invention, involving application of specially-tailored UV pulses, can produce a dramatic increase in the selectivity of a gas sensor (of the order of 1000 times). However, such a dramatic increase in selectivity is not needed in all applications. In some cases it may be sufficient to set the properties of the UV pulses so that a lesser increase in selectivity is obtained, which is still significant in the context of the specific application, even if this is not the maximal increase that could have been obtained for the given gas species and sensing material.

Although the above-described experiments were performed using a gas sensor including a single ZnO sensing layer, it is believed that the observed improvement in selectivity and sensitivity obtained by application of UV pulses is not specific to such gas sensors, but on the contrary would occur also in other architectures of chemoresistor gas sensor. Thus, it is proposed to apply the above-described technique in multi-storey devices according to the various embodiments of the invention described in this document and, more generally, in other chemoresistor-type gas sensors and gas sensors based on conducting polymers.

When the above-described technique is applied in the multi-storey sensor architectures described above, the UV pulses may be applied to one or more of the storeys in the sensor. When UV pulses whose properties have been set in view of improving detection of a specific target gas are applied to the sensing material (or, more generally to the selectively-activatable material) of a given storey in the sensor, then the illuminated material will have a stronger response to the target gas than would have been the case without UV illumination (or, indeed, UV illumination with other pulses or continuously). Accordingly, in the case where this storey includes measurement electrodes the strength of the signal measured in this storey of the sensor will change. Moreover, the gas that passes from this storey to a subsequent storey in the sensor will have undergone a larger modification by the current storey than would have been the case if the UV pulses had not been applied. Both of these effects can be used as sources of data to help characterise the gas sample under analysis.

It will be understood that when the above-described technique is applied in the multi-storey sensor architectures described above, the properties of the UV pulses may be set dependent on a target gas species which the gas sensor aims to detect or, if desired, dependent on an interfering gas species that the UV-illuminated storey of the gas sensor is designed to prevent from reaching a subsequent storey. If desired, both approaches may be used simultaneously in different storeys of the same gas sensor, although the size of the sensor is liable to increase if multiple UV sources are provided.

The present inventors have further realized that the set of measurements obtainable using gas sensors according to the invention, and indeed other semiconducting gas sensors, can be further enriched by making use of another phenomenon observed when UV pulses are applied to the gas sensors. More particularly, the inventors have observed that when the UV pulse is first switched on transient effects can be observed in the response of the sensing material and the transient effects are different when the sensing material is being exposed to different gas species. This phenomenon is illustrated by FIG. 18.

Figure 18A:
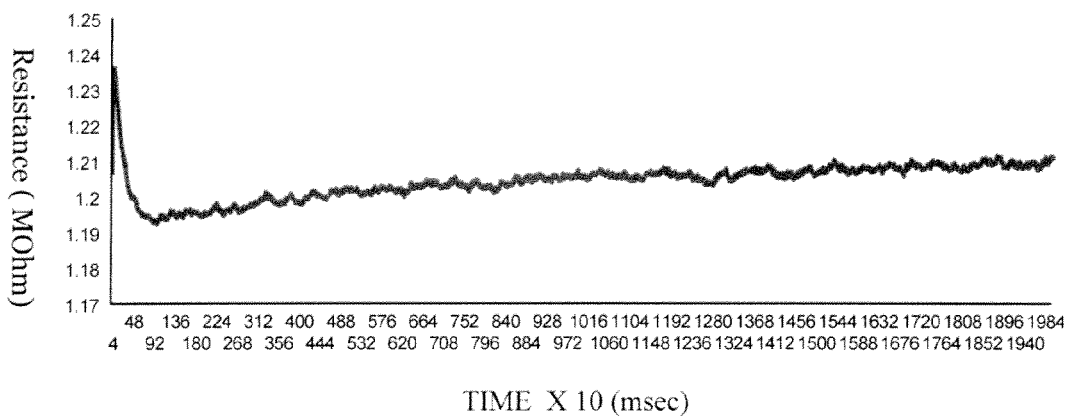
FIG. 18A shows sensor response during testing of a sample containing $H_2S$.
Figure 18B:
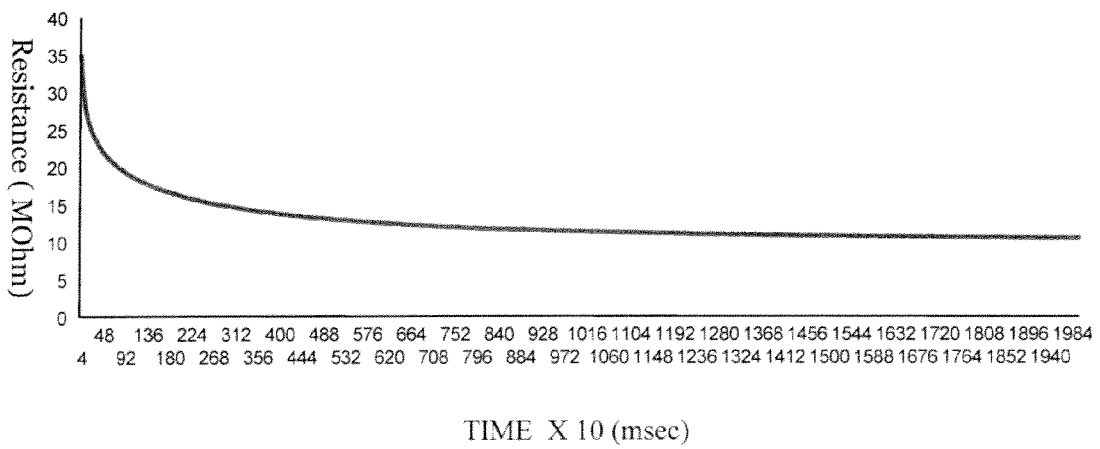
FIG. 18B shows sensor response during testing of a sample containing $NH_3$.
Figure 19A:
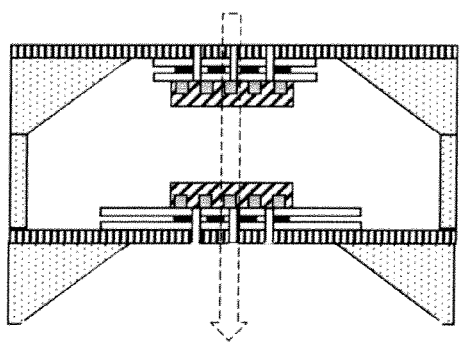
FIG. 19 illustrates various other architectures according to the first aspect of the invention, in which two sensing elements are mounted in series.
Figure 19B:
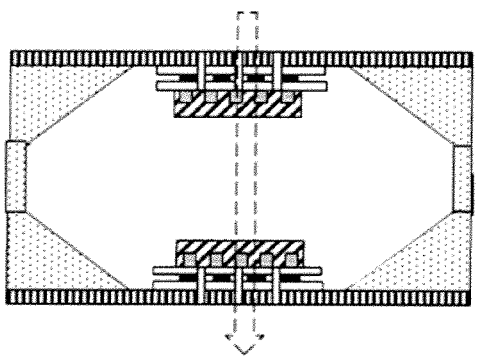
Figure 19C:
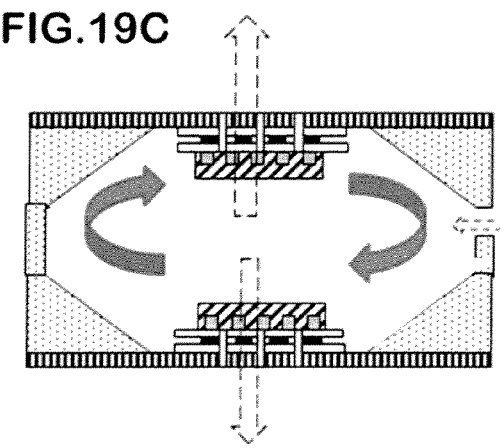
Figure 19D:
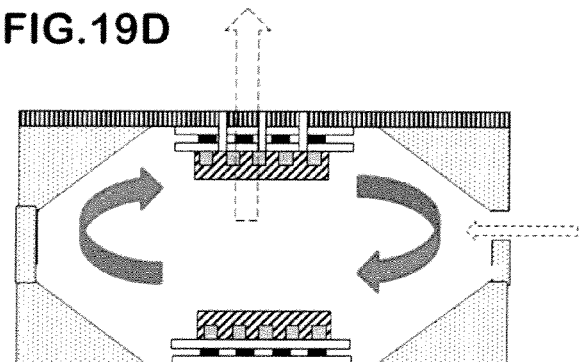

The traces shown in FIGS. 18A and 18B were measured during experiments performed using a test circuit comparable to that of FIG. 16B except that, in this case, the gas sensor was a two-storey sensor according to the first embodiment of the invention, in which the upper storey consisted of a micro-sensor with holes through the membrane and the lower storey consisted of a micro-sensor without holes in the membrane. In these experiments the two storeys of the micro-sensor both employed sensing layers made of ZnO, the upper storey using ZnO nanoparticles and the lower storey using ZnO nanorods. A stream of gas was made to flow continuously through the sensor at a rate of 200 $cm^3$ per minute: first a stream of air (for 2400 seconds), then a gas sample containing $H_2S$ at 1 ppm (for 1200 seconds), then air again (for 2400 seconds), followed by a gas sample containing $NH_3$ at 1 ppm (for 1200 seconds), and finally air (for 2400 seconds). The relative humidity of the gas was 50% in each case.

During each time period when the gas sensor was exposed to a new gas there were three measurement phases starting 100, 400 and 700 seconds before the changeover to the next gas, and each measurement phase lasted 20 seconds. During each measurement phase the sensor was exposed in a continuous fashion to UV light having a wavelength of 365 nm and the sensor response was measured every 10 milliseconds: the start and end of UV exposure was synchronised with the start and end of the measurement phase and the first measurement took place 10 milliseconds after the start of UV exposure. Accordingly, 2000 measurements were made during each measurement phase and each period of UV exposure was 20 seconds long.

FIG. 18A illustrates the response of the upper storey of the gas sensor during a typical one of the measurement phases that was performed while $H_2S$ was flowing through the sensor. FIG. 18B illustrates the response of the upper storey of the gas sensor during a typical one of the measurement phases that was performed while $NH_3$ was flowing through the sensor.

It can be seen from FIG. 18A that while the sensing material is being exposed to $H_2S$ there is a transient spike in the sensor response just after UV exposure begins, and the sensor resistance at the end of the spike (right-hand side of the spike as shown in FIG. 18A) is lower than the value at the start of the increase (left-hand side of the spike). Subsequently, the resistance value increases relatively slowly, while showing rapid short-term fluctuations.

In contrast, FIG. 18B shows that while the sensing material is being exposed to $NH_3$ the sensor response just after UV exposure begins has a sharp drop in resistance, and this fall in resistance continues smoothly, at a decreasing rate, as time goes on.

It is believed that the transient effects observed in the response of the sensing material at the onset of UV exposure are characteristic of the respective gas species to which the sensing material is being exposed, thus providing a tool for detecting specific substances.

One technique for exploiting the above-described phenomenon is, as follows. During a preliminary learning phase a selected sensing material is exposed to a set of one or more test substances and the transient effects observed in the response of the sensing material to the respective test substance(s) when UV exposure begins are measured. Discriminant analysis techniques are then used to determine the distinctive features of the transient effects that enable the test substance(s) to be characterised. During a subsequent measurement phase, the selected sensing material is exposed to a gas sample and, during the period of exposure, UV illumination is switched on. The response of the sensing material is measured so that the transient effects can be analysed and a comparative analysis can be performed with the transient effects measured for the set of test substances. This enables a specific test substance to be detected if it is present in the gas sample under analysis.

In the experiments described above with reference to FIG. 18, the sensor response at the onset of UV illumination was monitored over an extended period of time (20 seconds) so as to ensure that a complete picture was obtained of the reaction of the sensing material to the UV illumination. However, it will be observed from FIGS. 18A and 18B that significant transient effects occur within a very short time period following switching on of the ultraviolet illumination, notably within the first tenths of a second after onset of UV illumination. Accordingly, certain systems and methods embodying this aspect of the invention are designed to give fast results by basing the detection and/or identification of a target gas on processing of the first part of the sensing material's transient response, i.e. the response during the first second after onset of UV illumination.

In the first embodiment of the invention, described above with reference to FIGS. 3 to 11, the sensing layers of each storey have respective measurement electrodes, so each storey can produce an electrical signal that contributes to gas discrimination. A specific advantage of gas sensors according to the first embodiment of the invention is that the sensors in the multi-storey architecture can be: controlled, dynamically driven and acquire data individually.

A second embodiment of the invention will now be described with reference to FIGS. 12 to 15. According to the second embodiment of the invention a multi-storey chemoresistor type gas sensor is constructed by providing, in opposed relation to a chemoresistor type gas-sensing element, a layer of material that can be activated, when desired, to alter the composition of the gas reaching the gas-sensing element.

Figure 12:
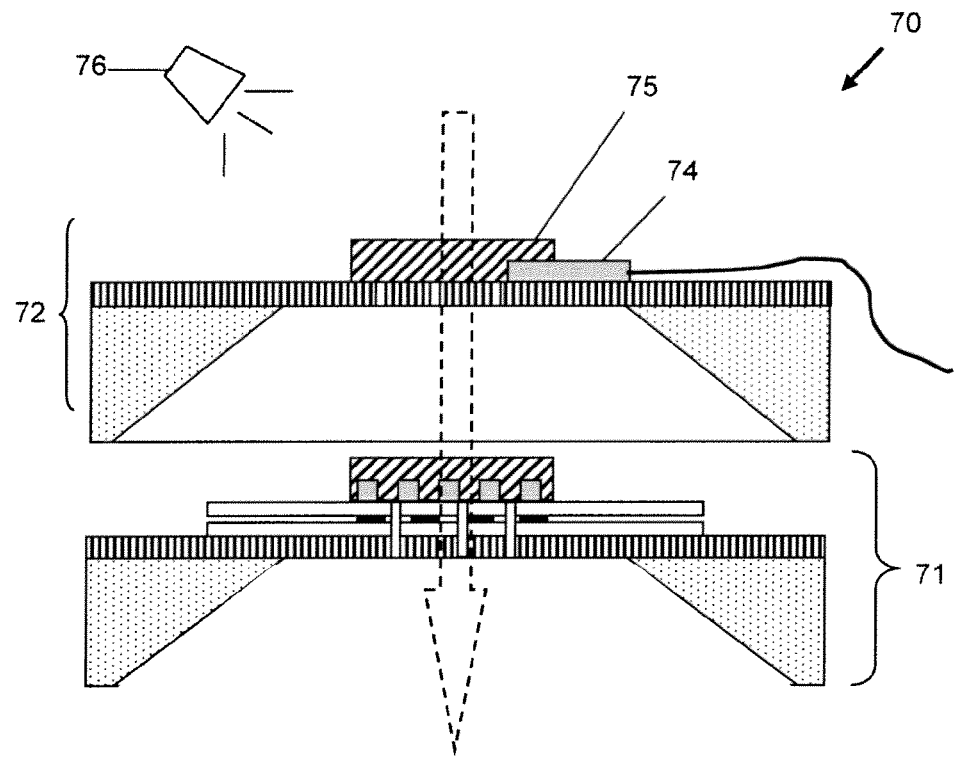
FIG. 12 is a schematic representation of a second embodiment of the invention, in which a chemoresistor type gas sensing element is arranged in series with a material that can be activated to change the character of the gas sensed by the gas sensing element.

FIG. 12 illustrates an example of a gas sensor architecture 70 according to the second embodiment of the invention. In the gas sensor 70 of FIG. 12 a gas-sensing element 71 has the same general structure as the gas sensing elements CH1, CH2 of FIGS. 3 to 5. However, in the second embodiment of the invention this gas-sensing element 71 is no longer arranged in series with a second gas-sensing element, instead it faces a second storey 72 which bears a layer of material 75 that can be selectively activated so as to change the gas sample before it reaches the sensing layer of the first storey 71. The material used for the layer 75 may be a semiconducting metal oxide of the same kind as the materials used for the sensing layers 52; it is also possible to use catalytic materials, for example $AuTiO_2$ or Pt.

As indicated by the arrow marked in dashed lines in FIG. 12, gas flows through the selectively-activatable material 75 of the second storey 72 before reaching the sensing layer of the first storey 71. The layer(s) supporting the selectively-activatable material 75 of the second storey 72 is (are) porous or provided with suitable holes (e.g. holes 58 as in the first embodiment) to allow passage of the gas. Accordingly, if the selectively-activatable material is activated, for example using a heater 74 or an ultraviolet light from a source 76 (or any other technique appropriate to the nature of the material forming the layer 75), then the gas sample will be changed before it reaches the first storey 71.

It could be considered that the second storey 72 functions rather like a catalytic filter, but an active catalytic filter that can be switched on and off. Although it is known to use filters in association with semi-conducting metal-oxide gas sensors, the known filters tend to be of one of two kinds: either filters which operate rather like a sieve, physically blocking the passage of larger gas molecules, or filters which consist of a layer of material deposited directly on the sensing layer and activated whenever the sensing layer is activated (e.g. by a heater). In the second embodiment of the invention the selectively-activatable material 75 of the second storey can be activated independently of the activation of the sensing layer of the first storey 71.

One advantage provided by the second embodiment of the invention is that it provides an additional technique for increasing the number of measurements that can be taken by the gas-sensing element 71 of the first storey. More particularly, the response of the sensing layer of the first storey 71 can be measured at times when the selectively-activatable layer 75 of the second storey is activated (possibly at multiple such times with other operating conditions being varied between each measurement) and at comparable times when this layer 75 is not activated. Accordingly, the analysis of the gas sample can be based on an increased range of parameters, which tends to improve the accuracy of the results.

Unlike devices according to the first embodiment of the invention, in devices according to the second embodiment of the invention no electrical signal is output by the storey that bears the layer 75 of selectively-activatable material. However, the materials specified for use in the layer 75 can show very good functionality for chemical filtering. Moreover, in this case there is no need to fabricate a measurement electrode for the storey carrying layer 75 and so manufacturing costs are reduced.

In the second embodiment of the invention a multi-storey structure has a second storey 72 bearing a selectively-activatable layer 75 that is porous and gas undergoing analysis passes through the porous selectively-activatable layer 75 on the second storey 72 to reach a sensing element provided on the subsequent storey 71 of the device. Accordingly, the composition of the gas sample reaching that sensing element is influenced to a great extent by the material of the selectively-activatable layer 75 present on the preceding storey.

In the first and second embodiments of the invention as described so far, the gas flow path from one storey in the multi-storey architecture to the next is defined by holes/pores through the membrane 53 carrying the sensing material 52/selectively-activatable material 75, and the membrane 53 extends across the sensor so that there is no other gas flow path to the subsequent storey. This arrangement ensures that the gas passing to the subsequent storey is maximally affected by the sensing material 52/selectively-activatable material 75 of the preceding storey.

The present inventors have realized that a similar effect can be achieved, albeit to a lesser degree, even in variants of the first and second embodiments in which the gas undergoing analysis does not necessarily pass through the selectively-activatable layer but simply comes into contact with that layer, for example because there is less than a total seal between the successive storeys of the gas sensor and some gas reaches the subsequent storey without passing through the selectively-activatable layer of the preceding storey. Moreover, the inventors have devised variants of the second embodiment of the invention in which—even though the selectively-activatable material is located in the same chamber as the sensing material of the subsequent storey—the gas can be caused to be modified by the selectively-activatable layer before it comes into contact with the sensing layer of the subsequent storey. Accordingly, in these variants it may be considered that the gas passes in series from one storey to the next as in the earlier-described embodiments.

Figure 13:
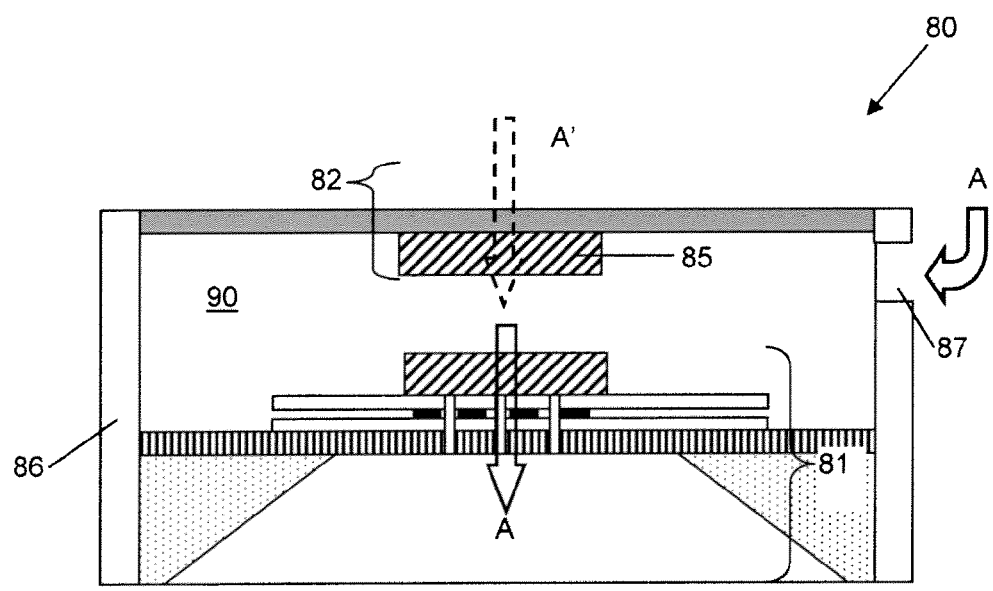
FIG. 13 is a schematic representation of a first variant of the second embodiment.

A first variant of the second embodiment is illustrated in FIG. 13. As can be seen from FIG. 13, according to the variant of the second embodiment a gas sensor 80 includes a housing 86 containing first and second storeys 81, 82 mounted to define a chamber 90 between them. The first storey 81 is a gas-sensing element comparable to one of the gas-sensing elements CH1, CH2 of FIGS. 3 and 4. The second storey 82 bears a layer 85 of selectively-activatable material comparable to that of FIG. 12 but, in the present case, the layer 85 is positioned inside the chamber 90 facing the sensing layer of the first storey 81.

In this first variant of the second embodiment, the second storey 82 may be porous, or provided with holes, so that the gas passes through the selectively-activatable material 85 as shown by the arrow A' marked in FIG. 13 using dashed lines. In such a case it is clear that the gas reaching the first storey 81 can be modified as its passes through the selectively-activatable material 85, notably by activating that material 85 (e.g. using an associated heater).

Alternatively (or additionally), the gas sample to be analysed may enter the chamber 90 through one or more openings 87 in the side wall of the housing, and exit the chamber 90 through the first storey 81, as indicated by the arrows A shown in FIG. 13. In this case, gas entering the chamber 90 through the opening 87 may still be modified to a useful extent by the selectively-activatable material 85 of the second storey 82 before it is detected by the sensing material of the first storey 81 by virtue of positioning the material 85 sufficiently close to the first storey 81 and/or suitable control of the flow rate of gas into/out of chamber 90 (as explained below).

Figure 14:
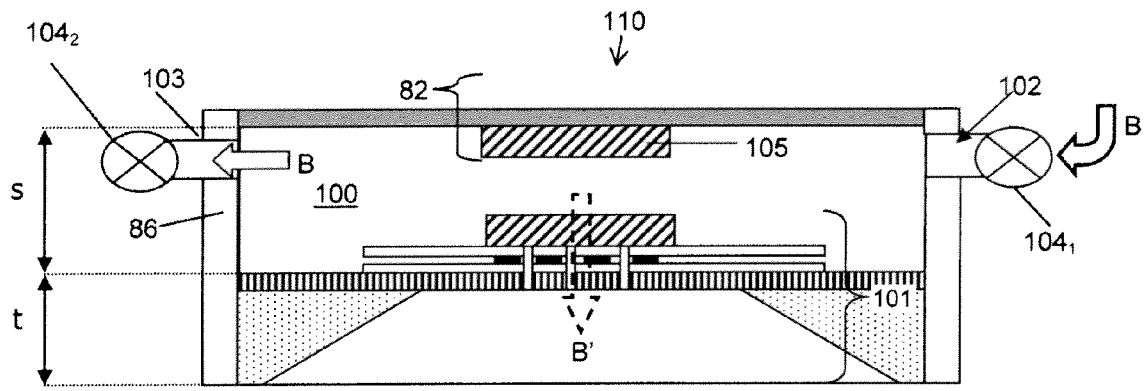
FIG. 14 is a schematic representation of a second variant of the second embodiment.

A second variant of the second embodiment is illustrated in FIG. 14. In this variant the gas is introduced inside the chamber 100 under the control of a valve 104$_1$ via a lateral opening 102 and can pass partially (B') though the first storey 101. As in the first variant of the second embodiment, the gas may be modified by the activation of catalytic materials 105, before it is detected by the sensing material in the first storey 101, by suitable control of the spacing between the catalytic material 105 and the first storey 101 and/or the gas flow rate. The gas exhaust is through an exit opening 103 under the control of a second valve 104$_2$.

This system can allow the flow rate B' through the sensor to be adjusted by control of the valves 104. Different patterns of gas flow are supported including gas flow controlled according to the following two patterns:

Pattern 1:
  a) introduce gas into chamber 100 by opening valve 104$_1$ while keeping valve 104$_2$ closed,
  b) close valve 104$_1$ and maintain gas in chamber 100 during a selected time period, (during this period some gas species will exit the chamber 100 via the sensor 101, as indicated by arrow B'),
  c) open valve 104$_2$ to empty chamber 100, and
  d) repeat steps a)-c) as desired.

If desired, the emptying of the chamber 100 in step c) can be accompanied by (and/or followed by) the passage of a cleaning gas, e.g. air, through the chamber, before a new sample is introduced.

Typically, all the desired measurements in relation to a given gas sample are taken while it is resident in the chamber during a single one of the residence periods mentioned in step b) above; this reduces the risk that operating conditions may vary, independently of the operator's control, between different measurements taken in relation to a given gas sample. Depending on the gases under analysis and the sensing materials in question, this will typically require a residence time of between 1 second and several minutes in the chamber 100.

However, it is not essential to perform all measurements during a single residence period; if desired, successive portions of a gas sample may be introduced into the chamber during different instances of step b), notably during successive instances of step b).

Pattern 2:

Allow gas to flow continuously through the device during the measurement period. During continuous gas flow, control the opening amount of valves $104_1$ and $104_2$ to obtain a desired volume of gas flowing through the device each minute. The gas flows, primarily, from 102 to 103 when valve $104_2$ is open, but a portion flows through sensor 101 (arrow B' in FIG. 14). Advantageously, the flow rate through valve $104_2$ is set sufficiently low to allow homogenization of the gas in chamber 100.

Typically, when the thickness of the wafer (dimension t in FIG. 14) is about 0.5 mm, useful modification of the gas by the catalytic material 105 is obtained when the distance between the storeys (dimension s in FIG. 14) is in the range of about 0.5 mm to about 3 mm—corresponding to a volume of $2 \times s$ mm$^3$ (i.e. about 1 mm$^3$ to about 6 mm$^3$)—for gas flow according to Pattern 1 when the gas is held in chamber 100 for a period in the range of about 1 second to 30 seconds, and for gas flow according to Pattern 2 when the gas flow rate from 102 to 103 during continuous gas flow is in the range of about 1 ml per minute to about 20 ml per minute.

Figure 15:
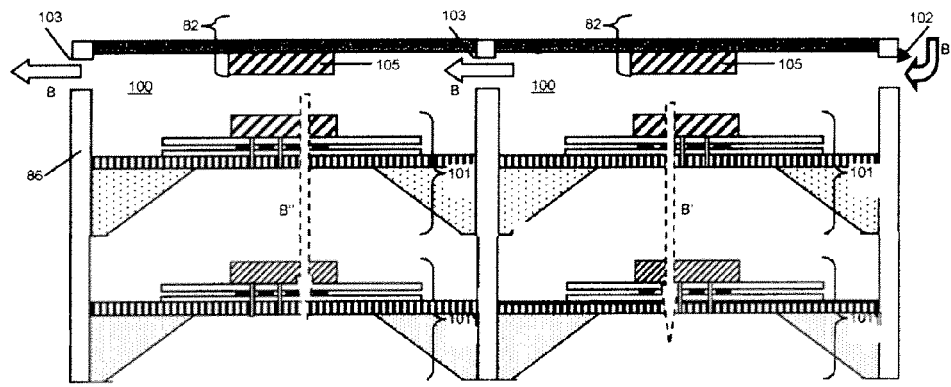
FIG. 15 is a schematic representation of a third variant of the second embodiment.

FIG. 15 shows a third variant; this is a typical example of an assembly in which global flow B is not limited and CH1 CH2 cells with partial Flows B' and B" allow measurement of the gas. As in the first and second variants of the second embodiment, the gas may be modified by the activation of catalytic materials 105, before it is detected by the sensing material in the first storey 101, by suitable control of the spacing between the catalytic material 105 and the first storey 101 and/or of the gas flow rate.

Arranging the selectively-activatable material of the top storey on the opposite side of a common chamber from the bottom sensor, as shown in FIGS. 13 to 15, can be useful for promoting catalytic combustion of target gas because the contact surface area of gas enlarges. As a result, the combustion time can be monitored to discriminate gases. This technique can be applied also in the first embodiment of the invention to produce equivalent advantages.

It will readily be understood that the first and second embodiments of the invention can be combined, notably to produce a stacked structure in which some storeys have sensing layers equipped with measurement electrodes and one or more other storeys bear sensing layers without measurement electrodes.

FIG. 19 illustrates some other configurations of gas sensors according to the first aspect of the present invention, in which two gas-sensing elements are mounted in series. It will be understood that the configurations illustrated in FIG. 19 may be extended by adding other storeys and that, once again, such extended structures may include additional storeys have sensing layers equipped with measurement electrodes and/or storeys bear sensing layers without measurement electrodes, as desired. The curved arrows in FIGS. 19C and D indicate circular flow, and preferably vortex flow, designed to ensure that each storey in the device affects the gas sensed by the other storey (bearing in mind that the activation of the different storeys will be controlled so that they are not necessarily activated at the same time).

Although the present invention has been described above with reference to particular embodiments, the skilled person will readily understand that the present invention is not limited by the details of the above-described embodiments. More particularly, the skilled person will understand that various modifications and developments can be made in the above-described embodiments and that different embodiments can be designed without departing from the present invention as defined in the appended claims.

For example, although the specific embodiments described above make use of a base substrate made of silicon it will readily be understood that other materials having adequate mechanical properties could be used instead: including but not limited to ceramic materials ($Al_2O_3$, etc.), glass, and plastics.

Furthermore, although the description above refers to the use of layers of catalytic materials, it is to be understood that the layers with or without measurement electrodes may be formed of "trap" materials, for example Tenax®, zeolites, activated charcoal, etc., and these materials may be passive (rapid trapping, slow release) or active (e.g. where desorption is produced using heating). It is to be understood that, in devices according to the first aspect of the invention, passive materials will be employed in architectures in which at least one storey includes a selectively-activatable layer.

Moreover, although the use of heating pulses to promote baseline return is described above in the context of a particular embodiment and aspect of the invention, it is to be understood that heating pulses may be employed for this purpose in the other embodiments and aspects of the invention.

Similarly, although the use of a cleansing flow of air (or other cleaning gas) through a chamber in a gas sensor is described above in the context of a particular aspect of the invention, it is to be understood that a cleaning phase of this type may be employed in the other embodiments and aspects of the invention. Furthermore, useful measurements may be taken during such a cleaning phase (as gas species desorb from the catalytic and/or sensing material layer(s)) and/or during phases where the gas sample is diluted.

What is claimed is:

1. A gas sensor of chemoresistor type having a multi-storey structure, the sensor comprising:
 a first storey comprising a sensing layer provided on an insulating layer, and measurement electrodes provided in contact with the sensing layer;
 a second storey comprising a support layer supporting a second sensing layer that is a layer of selectively-activatable material spaced from the sensing layer of the first storey, and second measurement electrodes in contact with said second sensing layer;
 wherein the first storey and the second storey each constitute a chemoresistor type gas sensing element, and
 an activation unit for controlling activation of the selectively-activatable layer;
 wherein the first and second storeys are arranged in series so that gas passes successively through the second storey to the first storey and the gas reaching the sensing layer of the first storey can be modified by activating the selectively-activatable material of the second storey.

2. A gas sensor according to claim 1, and comprising:
control means adapted to take measurements via the measurement electrodes of the first storey at times when the layer of selectively-activatable material of the second storey is activated and de-activated, respectively, and to process said measurements to discriminate a gas presented to the gas sensor.

3. A gas sensor according to claim 2, wherein:
holes or pores are formed through each storey for permitting the passage of gas from one storey to the next.

4. A gas sensor according to claim 3, comprising a stack of chemoresistor type gas sensing elements, wherein different materials form the respective sensing layers of at least two different storeys in the stack.

5. A gas sensor according to claim 3, wherein each gas sensing element has a micro-hotplate structure.

6. A gas sensor according to claim 2, wherein:
the first and second storeys define a chamber therebetween, and
the sensing layer of the first storey and the selectively-activatable layer of the second storey are disposed on opposed surfaces of the chamber.

7. A gas sensor according to claim 1, wherein:
holes or pores are provided through the second storey at least in a region where the selectively-activatable layer is provided, for permitting the passage of gas through the selectively-activatable layer of the second storey to the sensing layer of the first storey.

8. A gas sensor according to claim 2, wherein the activation unit comprises a heater.

9. A gas sensor according to claim 2, wherein the activation unit comprises a source of ultra-violet light operable to expose the selectively-activatable layer to pulses of ultraviolet light, and the gas sensor comprises a setting unit configured to control a duty ratio or duration of the ultraviolet light pulses applied by the source of ultraviolet light, in dependence on a target gas species to be detected by the gas sensor or an interfering gas species.

10. A gas sensor according to claim 2, wherein the activation unit comprises a source of ultraviolet light operable to expose a sensing layer in the gas sensor to pulses of ultraviolet light, and the gas sensor comprises a setting unit configured to control a duty ratio or duration of the ultraviolet light pulses applied by the source of ultraviolet light, in dependence on a target gas species to be detected by the gas sensor.

11. A gas sensor according to claim 1, comprising:
a source of ultraviolet light operable to expose one or more sensing layers in the sensor to ultraviolet light, and
an analysis unit configured to analyse measurements taken via measurement electrodes in contact with said one or more sensing layers to determine the transient response of said one or more sensing layers at onset of application of ultraviolet light.

* * * * *